US012648862B2

(12) United States Patent
Russell et al.

(10) Patent No.: US 12,648,862 B2
(45) **Date of Patent: \*Jun. 9, 2026**

(54) BONE JOINT INSERTER DEVICE AND METHODS OF USE THEREOF

(71) Applicant: SeaSpine Orthopedics Corporation, Carlsbad, CA (US)

(72) Inventors: Nicholas Alexander Russell, Carlsbad, CA (US); Robert Alan Hart, Portland, OR (US); Gregory Michael Mundis, San Diego, CA (US); Erik Christian Anders Olsson, Asheville, NC (US); Seth Kevin Williams, Madison, WI (US)

(73) Assignee: SeaSpine Orthopedics Corporation, Carlsbad, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/958,217

(22) Filed: Nov. 25, 2024

(65) Prior Publication Data

US 2025/0120826 A1 Apr. 17, 2025

Related U.S. Application Data

(63) Continuation of application No. 17/716,361, filed on Apr. 8, 2022, now Pat. No. 12,178,721.

(60) Provisional application No. 63/173,720, filed on Apr. 12, 2021.

(51) Int. Cl.
*A61F 2/46* (2006.01)

(52) U.S. Cl.
CPC .................................. *A61F 2/4611* (2013.01)

(58) Field of Classification Search
CPC ..... A61B 17/90; A61B 17/921; A61F 2/4611; A61F 2/46
USPC .................................. 606/61, 96, 98, 99, 104
See application file for complete search history.

(56) References Cited

U.S. PATENT DOCUMENTS

| | | | |
|---|---|---|---|
| 6,059,790 A | 5/2000 | Sand | |
| 6,083,225 A * | 7/2000 | Winslow | A61B 17/1757 606/279 |
| 6,423,073 B2 * | 7/2002 | Bowman | A61B 17/0401 606/88 |
| 7,597,695 B2 | 10/2009 | Schmiel et al. | |
| 7,708,761 B2 | 5/2010 | Petersen | |
| 7,837,713 B2 * | 11/2010 | Petersen | A61B 17/1757 606/247 |
| 7,901,439 B2 | 3/2011 | Horton | |
| 8,021,392 B2 | 9/2011 | Petersen | |
| 8,172,853 B2 | 5/2012 | Michelson | |
| 8,366,748 B2 | 2/2013 | Kleiner | |

(Continued)

FOREIGN PATENT DOCUMENTS

WO 2020061464 A1 3/2020

*Primary Examiner* — Jessica Weiss
(74) *Attorney, Agent, or Firm* — Dinsmore & Shohl LLP

(57) ABSTRACT

A bone joint inserter device for accessing and manipulating a facet joint is provided. The bone joint inserter device improves surgical control in bone anchor location, placement and insertion into target bone, while the inserter device also improves efficiency in engaging the target bone joint. The surgical instrument provides improved control of cutting device location and orientation, including directional control for precise bone anchor component insertion. Methods to use the bone joint inserter device in surgical procedures are also provided.

20 Claims, 17 Drawing Sheets

(56)            References Cited

U.S. PATENT DOCUMENTS

| | | |
|---|---|---|
| 8,623,054 B2 | 1/2014 | McCormack et al. |
| 8,740,912 B2 | 6/2014 | Stark |
| 8,753,345 B2 | 6/2014 | McCormack et al. |
| 8,753,347 B2 | 6/2014 | McCormack et al. |
| 8,834,472 B2 | 9/2014 | McCormack et al. |
| 8,870,882 B2 | 10/2014 | Kleiner |
| 9,011,492 B2 | 4/2015 | McCormack et al. |
| 9,060,748 B2 | 6/2015 | Housman et al. |
| 9,173,750 B2 | 11/2015 | Weiman et al. |
| 9,314,232 B2 | 4/2016 | Stark |
| 9,427,264 B2 | 8/2016 | Kleiner |
| 9,504,482 B2 | 11/2016 | Smith |
| 9,510,957 B2 | 12/2016 | Weiman et al. |
| 9,629,665 B2 | 4/2017 | McCormack et al. |
| 10,149,673 B2 | 12/2018 | McCormack et al. |
| 10,201,375 B2 | 2/2019 | McCormack et al. |
| 10,219,841 B1 | 3/2019 | Compton et al. |
| 10,398,573 B2 | 9/2019 | Duffield et al. |
| 10,456,175 B2 | 10/2019 | McCormack et al. |
| 10,548,744 B2 | 2/2020 | Weiman et al. |
| 10,568,666 B2 | 2/2020 | McCormack et al. |
| 10,588,672 B2 | 3/2020 | McCormack et al. |
| 10,682,150 B2 | 6/2020 | Stark |
| 10,682,243 B2 | 6/2020 | Phan et al. |
| 10,792,168 B2 | 10/2020 | Malcomson et al. |
| 11,141,144 B2 | 10/2021 | McCormack et al. |
| 2001/0016746 A1* | 8/2001 | McGuire ............... B25G 1/043 |
| | | 606/96 |

| | | |
|---|---|---|
| 2002/0198533 A1 | 12/2002 | Geisler et al. |
| 2004/0186482 A1* | 9/2004 | Kolb .................. A61B 17/1728 |
| | | 606/96 |
| 2006/0155283 A1* | 7/2006 | Doherty ............. A61B 17/8875 |
| | | 606/915 |
| 2010/0222829 A1 | 9/2010 | Petersen |
| 2010/0228253 A1* | 9/2010 | Plecko ............... A61B 17/1717 |
| | | 606/80 |
| 2012/0010620 A1 | 1/2012 | Petersen |
| 2012/0209386 A1* | 8/2012 | Triplett ................. A61F 2/4465 |
| | | 623/17.16 |
| 2014/0200668 A1* | 7/2014 | Kirschman .......... A61B 17/025 |
| | | 623/17.16 |
| 2015/0005883 A1* | 1/2015 | Weiman ................. A61F 2/4611 |
| | | 623/17.16 |
| 2016/0242754 A1 | 8/2016 | McCormack et al. |
| 2016/0249940 A1 | 9/2016 | Stark |
| 2017/0209158 A1 | 7/2017 | Williams |
| 2017/0367839 A1 | 12/2017 | Vestgaarden et al. |
| 2019/0262052 A1 | 8/2019 | Seifert et al. |
| 2020/0060733 A1 | 2/2020 | Compton et al. |
| 2020/0085475 A1 | 3/2020 | McCormack et al. |
| 2020/0138600 A1 | 5/2020 | Weiman et al. |
| 2020/0155205 A1 | 5/2020 | Tanaka et al. |
| 2020/0268396 A1 | 8/2020 | Stark |
| 2020/0315815 A1 | 10/2020 | Malcomson et al. |
| 2021/0386434 A1 | 12/2021 | Tanaka et al. |
| 2022/0031297 A1 | 2/2022 | McCormack et al. |

* cited by examiner

Figure 1

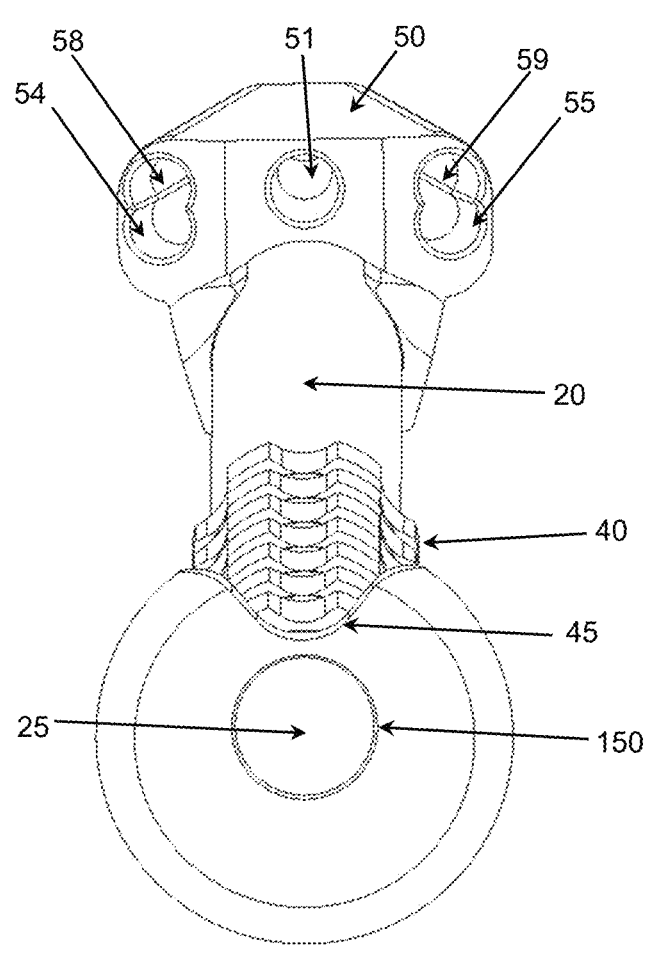

Figure 7a
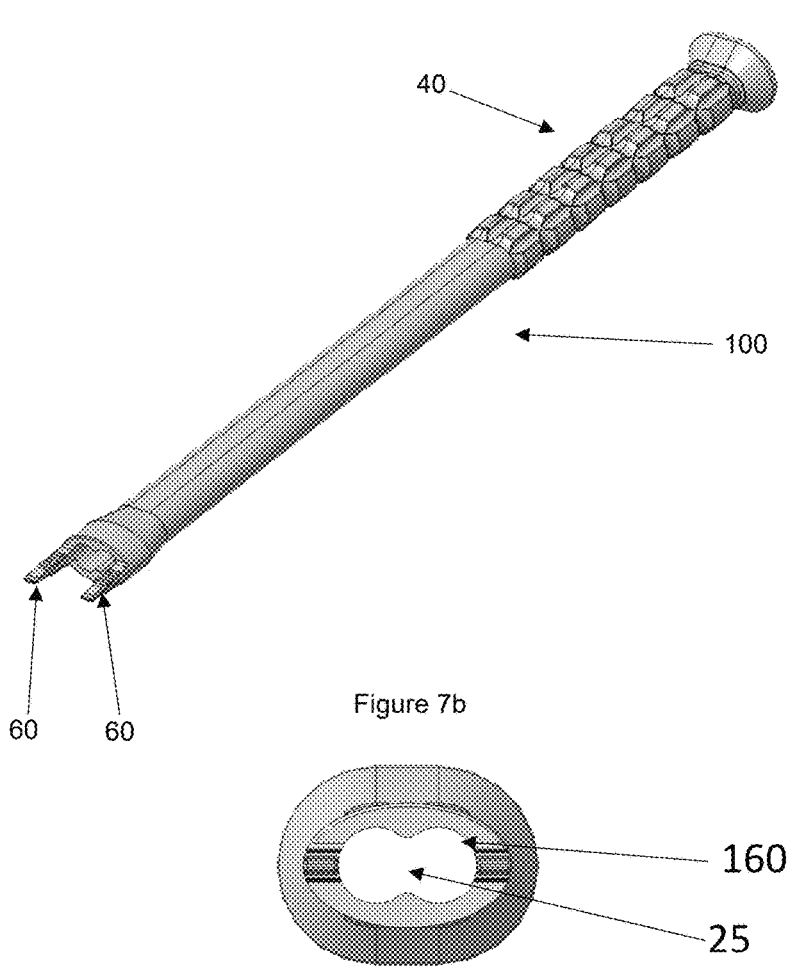
40
100
60        60
Figure 7b
160
25
Figure 7c
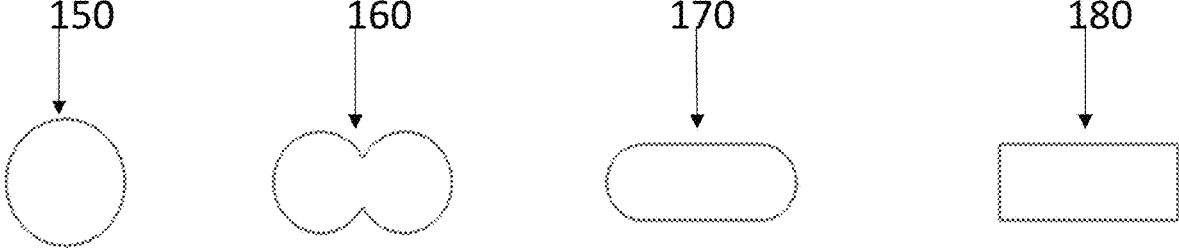
150          160          170          180

Figure 9
Upper Hole
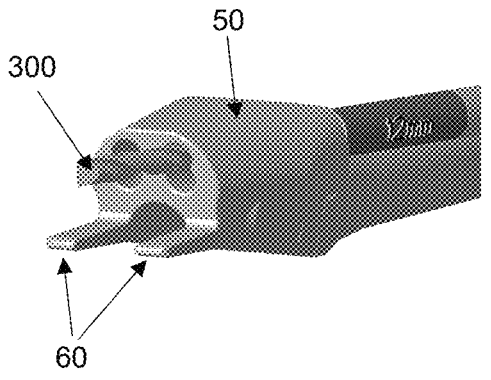
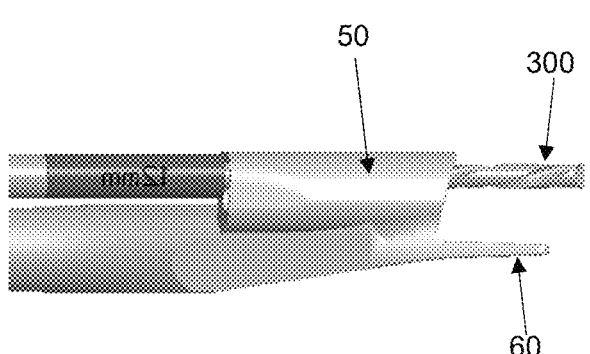
Lower Hole
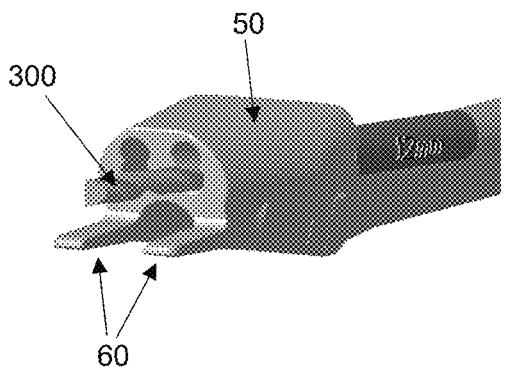
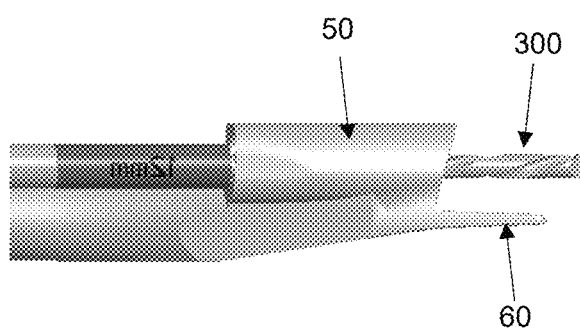

300

300

$d$

BONE JOINT INSERTER DEVICE AND METHODS OF USE THEREOF

CROSS-REFERENCE TO RELATED APPLICATIONS

Any and all applications for which a foreign or domestic priority claim is identified in the Application Data Sheet as filed with the present application are hereby incorporated by reference herein and made a part of the present disclosure.

FIELD OF THE INVENTION

The present disclosure provides a bone joint inserter device and methods of use. The device is particularly advantageous in that it streamlines surgical workflow to reduce surgical operation time, while providing flexibility and precision in placement of various types of anchoring devices in a vertebral lateral mass. The device further enhances engagement and manipulation of a vertebral facet joint in order to provide one or more anchoring devices along with delivery of various biological materials to the facet joint.

SUMMARY OF THE INVENTION

In one embodiment. the present invention provides a bone joint inserter device comprising: (a) a proximal section comprising an inserter head, wherein the inserter head comprises: (i) a face, wherein the face is configured to engage a bone surface; (ii) at least one prong, wherein the at least one prong is configured to engage a bone joint; (iii) a first channel comprising a first entry port and a first exit port, wherein the first entry port is at least as wide as the first exit port, and wherein the first channel is oriented at an acute angle relative to the center line of the inserter head; and (iv) a second channel comprising a second entry port and a second exit port, wherein the second entry port is at least as wide as the second exit port, and wherein the second channel is oriented at an acute angle relative to the center line of the inserter head; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In another embodiment, there is provided a bone joint inserter device as described herein, wherein the proximal section is fixedly interconnected to the shaft, and the shaft is fixedly interconnected to the distal section.

In still another embodiment, there is provided a bone joint inserter device as described herein, wherein the proximal section is fixedly interconnected to the shaft, and the shaft is removably interconnected to the distal section.

In yet another embodiment, there is provided a bone joint inserter device as described herein, wherein the proximal section is removably interconnected to the shaft, and the shaft is fixedly interconnected to the distal section.

In a further embodiment, there is provided a bone joint inserter device as described herein, wherein the proximal section is removably interconnected to the shaft, and the shaft is removably interconnected to the distal section.

In another embodiment, there is provided a bone joint inserter device as described herein, wherein the face is oriented perpendicular to the at least one prong.

In yet another embodiment, there is provided a bone joint inserter device as described herein, wherein the face is oriented at an acute angle relative to the at least one prong.

In still another embodiment, there is provided a bone joint inserter device as described herein, wherein the face is oriented at an obtuse angle relative to the at least one prong.

In a further embodiment, there is provided a bone joint inserter device as described herein, wherein the face comprises a surface texture selected from smooth, rough, irregular, knurled, stippled, toothed, and any combination thereof.

In another embodiment, there is provided a bone joint inserter device as described herein, wherein the face comprises a contact surface shape selected from flat, angled, curved, concave, convex, and a combination thereof.

In an embodiment, there is provided a bone joint inserter device as described herein, wherein the at least one prong extends from an inferior portion of the face.

In yet another embodiment, there is provided a bone joint inserter device as described herein, wherein the at least one prong extends from a superior portion of the face.

In still another embodiment, there is provided a bone joint inserter device as described herein, wherein the at least one prong extends from a midline portion of the face.

In a further embodiment, there is provided a bone joint inserter device as described herein, wherein the at least one prong comprises an end shape selected from pointed, tapered, beveled, chiseled, blunt, rounded, and square.

In another embodiment, there is provided a bone joint inserter device as described herein, wherein the at least one prong comprises a surface texture selected from smooth, corrugated, stippled, and knurled.

In yet another embodiment, there is provided a bone joint inserter device as described herein, wherein the surface texture is present on: the upper surface of the at least one prong; the lower surface of the at least one prong; or both the upper surface and lower surface of the at least one prong.

In a further embodiment, there is provided a bone joint inserter device as described herein, wherein the shaft comprises a textured surface selected from knurled, corrugated, stippled, and any combination thereof.

In still another embodiment, there is provided a bone joint inserter device as described herein, wherein the shaft comprises an ergonomic grip.

In an embodiment, there is provided a bone joint inserter device as described herein, wherein the distal portion comprises a notch for orienting a compatible device substantially parallel to the center line of the long axis of the inserter device In another embodiment, there is provided a bone joint inserter device as described herein, wherein the distal section comprises a lumen entry port shape selected from round, rectangular, square, and elliptical.

In yet another embodiment, there is provided a bone joint inserter device as described herein, wherein the first entry port is a slot, or wherein the second entry port is a slot, or wherein the first entry port and the second entry port are both a slot.

In still another embodiment, there is provided a bone joint inserter device as described herein, wherein the width of the first entry port is wider than the first exit port.

In another embodiment, there is provided a bone joint inserter device as described herein, wherein the width of the second entry port is wider than the second exit port.

In a further embodiment, there is provided a bone joint inserter device as described herein, wherein the width of the first entry port is wider than the first exit port, and the width of the second entry port is wider than the second exit port.

In yet another embodiment, there is provided a bone joint inserter device as described herein, wherein the first entry port comprises two holes.

In an embodiment, there is provided a bone joint inserter device as described herein, wherein the second entry port comprises two holes.

In another embodiment, there is provided a bone joint inserter device as described herein, wherein the first entry port comprises two holes, and the second entry port comprises two holes.

In still another embodiment, there is provided a bone joint inserter device as described herein, wherein the two holes of the first entry port are arranged in a vertically stacked configuration.

In a further embodiment, there is provided a bone joint inserter device as described herein, wherein the two holes of the second entry port are arranged in a vertically stacked configuration.

In yet another embodiment, there is provided a bone joint inserter device as described herein, wherein the two holes of the first entry port are arranged in a vertically stacked configuration, and the two holes of the second entry port are arranged in a vertically stacked configuration.

In another embodiment, there is provided a bone joint inserter device as described herein, wherein the two holes of the first entry port are arranged in a horizontally stacked configuration.

In still another embodiment, there is provided a bone joint inserter device as described herein, wherein the two holes of the second entry port are arranged in a horizontally stacked configuration.

In an embodiment, there is provided a bone joint inserter device as described herein, wherein the two holes of the first entry port are arranged in a horizontally stacked configuration, and the two holes of the second entry port are arranged in a horizontally stacked configuration.

In another embodiment, there is provided a bone joint inserter device as described herein, wherein the bone joint is a cervical facet joint.

In still another embodiment, there is provided a bone joint inserter device comprising: (a) a proximal section comprising an inserter head, wherein the inserter head comprises: (i) a superior portion comprising a face, wherein the face is configured to engage a bone surface; (ii) an inferior portion comprising at least one prong, wherein the at least one prong is configured to engage a bone joint; (iii) a first channel comprising a first entry port and a first exit port, wherein the first entry port is at least as wide as the first exit port, and wherein the first channel is oriented at an acute angle relative to the center line of the inserter head; and (iv) a second channel comprising a second entry port and a second exit port, wherein the second entry port is at least as wide as the second exit port, and wherein the second channel is oriented at an acute angle relative to the center line of the inserter head; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In yet another embodiment, there is provided a bone joint inserter device as described herein, wherein the proximal section is fixedly interconnected to the shaft, and the shaft is fixedly interconnected to the distal section.

In a further embodiment, there is provided a bone joint inserter device as described herein, wherein the proximal section is fixedly interconnected to the shaft, and the shaft is removably interconnected to the distal section.

In an embodiment, there is provided a bone joint inserter device as described herein, wherein the proximal section is removably interconnected to the shaft, and the shaft is fixedly interconnected to the distal section.

In another embodiment, there is provided a bone joint inserter device as described herein, wherein the proximal section is removably interconnected to the shaft, and the shaft is removably interconnected to the distal section.

In yet another embodiment, there is provided a bone joint inserter device as described herein, wherein the face is oriented perpendicular to the at least one prong.

In a further embodiment, there is provided a bone joint inserter device as described herein, wherein the face is oriented at an acute angle relative to the at least one prong.

In still another embodiment, there is provided a bone joint inserter device as described herein, wherein the face is oriented at an obtuse angle relative to the at least one prong.

In an embodiment, there is provided a bone joint inserter device as described herein, wherein the face comprises a surface texture selected from smooth, rough, irregular, knurled, stippled, toothed, and any combination thereof.

In another embodiment, there is provided a bone joint inserter device as described herein, wherein the face comprises a contact surface shape selected from flat, angled, curved, concave, convex, and a combination thereof.

In still another embodiment, there is provided a bone joint inserter device as described herein, wherein the at least one prong extends from an inferior portion of the face.

In yet another embodiment, there is provided a bone joint inserter device as described herein, wherein the at least one prong extends from a superior portion of the face.

In a further embodiment, there is provided a bone joint inserter device as described herein, wherein the at least one prong extends from a midline portion of the face.

In another embodiment, there is provided a bone joint inserter device as described herein, wherein the at least one prong comprises an end shape selected from pointed, tapered, beveled, chiseled, blunt, rounded, and square.

In an embodiment, there is provided a bone joint inserter device as described herein, wherein the at least one prong comprises a surface texture selected from smooth, corrugated, stippled, and knurled.

In another embodiment, there is provided a bone joint inserter device as described herein, wherein the surface texture is present on: the upper surface of the at least one prong; the lower surface of the at least one prong; or both the upper surface and lower surface of the at least one prong.

In yet another embodiment, there is provided a bone joint inserter device as described herein, wherein the shaft comprises a textured surface selected from knurled, corrugated, stippled, and any combination thereof.

In a further embodiment, there is provided a bone joint inserter device as described herein, wherein the shaft comprises an ergonomic grip.

In still another embodiment, there is provided a bone joint inserter device as described herein, wherein the distal portion comprises a notch for orienting a compatible device substantially parallel to the center line of the long axis of the inserter device.

In an embodiment, there is provided a bone joint inserter device as described herein, wherein the distal section comprises a lumen entry port shape selected from round, rectangular, square, and elliptical.

In another embodiment, there is provided a bone joint inserter device as described herein, wherein the first entry port is a slot.

In yet another embodiment, there is provided a bone joint inserter device as described herein, wherein the second entry port is a slot.

In still another embodiment, there is provided a bone joint inserter device as described herein, wherein the first entry port and the second entry port are both a slot.

In a further embodiment, there is provided a bone joint inserter device as described herein, wherein the width of the first entry port is wider than the first exit port.

In another embodiment, there is provided a bone joint inserter device as described herein, wherein the width of the second entry port is wider than the second exit port.

In an embodiment, there is provided a bone joint inserter device as described herein, wherein the width of the first entry port is wider than the first exit port, and the width of the second entry port is wider than the second exit port.

In another embodiment, there is provided a bone joint inserter device as described herein, wherein the first entry port comprises two holes.

In still another embodiment, there is provided a bone joint inserter device as described herein, wherein the second entry port comprises two holes.

In yet another embodiment, there is provided a bone joint inserter device as described herein, wherein the first entry port comprises two holes, and the second entry port comprises two holes.

In another embodiment, there is provided a bone joint inserter device as described herein, wherein the two holes of the first entry port are arranged in a vertically stacked configuration.

In an embodiment, there is provided a bone joint inserter device as described herein, wherein the two holes of the second entry port are arranged in a vertically stacked configuration.

In another embodiment, there is provided a bone joint inserter device as described herein, wherein the two holes of the first entry port are arranged in a vertically stacked configuration, and the two holes of the second entry port are arranged in a vertically stacked configuration.

In still another embodiment, there is provided a bone joint inserter device as described herein, wherein the two holes of the first entry port are arranged in a horizontally stacked configuration.

In another embodiment, there is provided a bone joint inserter device as described herein, wherein the two holes of the second entry port are arranged in a horizontally stacked configuration.

In another embodiment, there is provided a bone joint inserter device as described herein, wherein the two holes of the first entry port are arranged in a horizontally stacked configuration, and the two holes of the second entry port are arranged in a horizontally stacked configuration.

In another embodiment, there is provided a bone joint inserter device as described herein, wherein the bone joint is a cervical facet joint.

In an embodiment, there is provided a facet joint inserter device comprising: (a) a proximal section comprising an inserter head, wherein the inserter head comprises: (i) a superior portion comprising a face, wherein the face is configured to engage a bone surface; (ii) an inferior portion comprising at least two prongs, wherein the at least two prongs are configured to engage a spinal vertebral joint; (iii) a first channel comprising a first entry port and a first exit port, wherein the first entry port is at least as wide as the first exit port, and wherein the first channel is oriented at an acute angle relative to the center line of the inserter head; and (iv) a second channel comprising a second entry port and a second exit port, wherein the second entry port is at least as wide as the second exit port, and wherein the second channel is oriented at an acute angle relative to the center line of the inserter head; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In another embodiment, there is provided a bone joint inserter device as described herein, wherein the proximal section is fixedly interconnected to the shaft, and the shaft is fixedly interconnected to the distal section.

In still another embodiment, there is provided a bone joint inserter device as described herein, wherein the proximal section is fixedly interconnected to the shaft, and the shaft is removably interconnected to the distal section.

In another embodiment, there is provided a bone joint inserter device as described herein, wherein the proximal section is removably interconnected to the shaft, and the shaft is fixedly interconnected to the distal section.

In another embodiment, there is provided a bone joint inserter device as described herein, wherein the proximal section is removably interconnected to the shaft, and the shaft is removably interconnected to the distal section.

In another embodiment, there is provided a bone joint inserter device as described herein, wherein the face is oriented perpendicular to the at least one prong.

In another embodiment, there is provided a bone joint inserter device as described herein, wherein the face is oriented at an acute angle relative to the at least one prong.

In another embodiment, there is provided a bone joint inserter device as described herein, wherein the face is oriented at an obtuse angle relative to the at least one prong.

In another embodiment, there is provided a bone joint inserter device as described herein, wherein the face comprises a surface texture selected from smooth, rough, irregular, knurled, stippled, toothed, and any combination thereof.

In still another embodiment, there is provided a bone joint inserter device as described herein, wherein the face comprises a contact surface shape selected from flat, angled, curved, concave, convex, and a combination thereof.

In another embodiment, there is provided a bone joint inserter device as described herein, wherein the at least two prongs extend from an inferior portion of the face.

In another embodiment, there is provided a bone joint inserter device as described herein, wherein the at least two prongs extend from a superior portion of the face.

In another embodiment, there is provided a bone joint inserter device as described herein, wherein the at least two prongs extend from a midline portion of the face.

In still another embodiment, there is provided a bone joint inserter device as described herein, wherein each of the at least two prongs independently comprises an end shape selected from pointed, tapered, beveled, chiseled, blunt, rounded, and square.

In another embodiment, there is provided a bone joint inserter device as described herein, wherein the at least two prongs comprise a surface texture selected from smooth, corrugated, stippled, and knurled.

In another embodiment, there is provided a bone joint inserter device as described herein, wherein the surface texture is present on: the upper surface of the at least two prongs; the lower surface of the at least two prongs; or both the upper surface and lower surface of the at least two prongs.

In another embodiment, there is provided a bone joint inserter device as described herein, wherein the shaft comprises a textured surface selected from knurled, corrugated, stippled, and any combination thereof.

In still another embodiment, there is provided a bone joint inserter device as described herein, wherein the shaft comprises an ergonomic grip.

In another embodiment, there is provided a bone joint inserter device as described herein, wherein the distal portion comprises a notch for orienting a compatible device substantially parallel to the center line of the long axis of the inserter device In another embodiment, there is provided a bone joint inserter device as described herein, wherein the distal section comprises a lumen entry port shape selected from round, rectangular, square, and elliptical.

In another embodiment, there is provided a bone joint inserter device as described herein, wherein the first entry port is a slot.

In still another embodiment, there is provided a bone joint inserter device as described herein, wherein the second entry port is a slot.

In another embodiment, there is provided a bone joint inserter device as described herein, wherein the first entry port and the second entry port are both a slot.

In another embodiment, there is provided a bone joint inserter device as described herein, wherein the width of the first entry port is wider than the first exit port.

In another embodiment, there is provided a bone joint inserter device as described herein, wherein the width of the second entry port is wider than the second exit port.

In still another embodiment, there is provided a bone joint inserter device as described herein, wherein the width of the first entry port is wider than the first exit port, and the width of the second entry port is wider than the second exit port.

In another embodiment, there is provided a bone joint inserter device as described herein, wherein the first entry port comprises two holes.

In another embodiment, there is provided a bone joint inserter device as described herein, wherein the second entry port comprises two holes.

In still another embodiment, there is provided a bone joint inserter device as described herein, wherein the first entry port comprises two holes, and the second entry port comprises two holes.

In another embodiment, there is provided a bone joint inserter device as described herein, wherein the two holes of the first entry port are arranged in a vertically stacked configuration.

In another embodiment, there is provided a bone joint inserter device as described herein, wherein the two holes of the second entry port are arranged in a vertically stacked configuration.

In another embodiment, there is provided a bone joint inserter device as described herein, wherein the two holes of the first entry port are arranged in a vertically stacked configuration, and the two holes of the second entry port are arranged in a vertically stacked configuration.

In still another embodiment, there is provided a bone joint inserter device as described herein, wherein the two holes of the first entry port are arranged in a horizontally stacked configuration.

In another embodiment, there is provided a bone joint inserter device as described herein, wherein the two holes of the second entry port are arranged in a horizontally stacked configuration.

In yet another embodiment, there is provided a bone joint inserter device as described herein, wherein the two holes of the first entry port are arranged in a horizontally stacked configuration, and the two holes of the second entry port are arranged in a horizontally stacked configuration.

In a further embodiment, there is provided a bone joint inserter device as described herein, wherein the bone joint is a cervical facet joint.

In another embodiment, there is provided a bone joint inserter device comprising: (a) a proximal section comprising an inserter head, wherein the inserter head comprises: (i) a superior portion comprising a face, wherein the face is configured to engage a bone surface; (ii) an inferior portion comprising at least one prong, wherein the at least one prong is configured to engage a bone joint; (iii) a first channel comprising a first entry port and a first exit port, wherein the first entry port is at least as wide as the first exit port, and wherein the first channel is oriented at an acute angle relative to the center line of the inserter head; (iv) a second channel comprising a second entry port and a second exit port, wherein the second entry port is at least as wide as the second exit port, and wherein the second channel is oriented at an acute angle relative to the center line of the inserter head; and (v) a center channel comprising a central entry port and a central exit port, wherein the central entry port is at least as wide as the central exit port, and wherein the center channel is disposed between the first channel and the second channel; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In still another embodiment, there is provided a bone joint inserter device as described herein, wherein the proximal section is fixedly interconnected to the shaft, and the shaft is fixedly interconnected to the distal section.

In another embodiment, there is provided a bone joint inserter device as described herein, wherein the proximal section is fixedly interconnected to the shaft, and the shaft is removably interconnected to the distal section.

In another embodiment, there is provided a bone joint inserter device as described herein, wherein the proximal section is removably interconnected to the shaft, and the shaft is fixedly interconnected to the distal section.

In another embodiment, there is provided a bone joint inserter device as described herein, wherein the proximal section is removably interconnected to the shaft, and the shaft is removably interconnected to the distal section.

In still another embodiment, there is provided a bone joint inserter device as described herein, wherein the face is oriented perpendicular to the at least one prong.

In another embodiment, there is provided a bone joint inserter device as described herein, wherein the face is oriented at an acute angle relative to the at least one prong.

In another embodiment, there is provided a bone joint inserter device as described herein, wherein the face is oriented at an obtuse angle relative to the at least one prong.

In another embodiment, there is provided a bone joint inserter device as described herein, wherein the face comprises a surface texture selected from smooth, rough, irregular, knurled, stippled, toothed, and any combination thereof.

In still another embodiment, there is provided a bone joint inserter device as described herein, wherein the face comprises a contact surface shape selected from flat, angled, curved, concave, convex, and a combination thereof.

In another embodiment, there is provided a bone joint inserter device as described herein, wherein the at least one prong extends from an inferior portion of the face.

In another embodiment, there is provided a bone joint inserter device as described herein, wherein the at least one prong extends from a superior portion of the face.

In another embodiment, there is provided a bone joint inserter device as described herein, wherein the at least one prong extends from a midline portion of the face.

In another embodiment, there is provided a bone joint inserter device as described herein, wherein the at least one prong comprises an end shape selected from pointed, tapered, beveled, chiseled, blunt, rounded, and square.

In still another embodiment, there is provided a bone joint inserter device as described herein, wherein the at least one prong comprises a surface texture selected from smooth, corrugated, stippled, and knurled.

In another embodiment, there is provided a bone joint inserter device as described herein, wherein the surface texture is present on: the upper surface of the at least one prong; the lower surface of the at least one prong; or both the upper surface and lower surface of the at least one prong.

In a further embodiment, there is provided a bone joint inserter device as described herein, wherein the shaft comprises a textured surface selected from knurled, corrugated, stippled, and any combination thereof.

In another embodiment, there is provided a bone joint inserter device as described herein, wherein the shaft comprises an ergonomic grip.

In still another embodiment, there is provided a bone joint inserter device as described herein, wherein the distal portion comprises a notch for orienting a compatible device substantially parallel to the center line of the long axis of the inserter device In another embodiment, there is provided a bone joint inserter device as described herein, wherein the distal section comprises a lumen entry port shape selected from round, rectangular, square, and elliptical.

In yet another embodiment, there is provided a bone joint inserter device as described herein, wherein the first entry port is a slot.

In another embodiment, there is provided a bone joint inserter device as described herein, wherein the second entry port is a slot.

In still another embodiment, there is provided a bone joint inserter device as described herein, wherein the first entry port and the second entry port are both a slot.

In an embodiment, there is provided a bone joint inserter device as described herein, wherein the width of the first entry port is wider than the first exit port.

In another embodiment, there is provided a bone joint inserter device as described herein, wherein the width of the second entry port is wider than the second exit port.

In yet another embodiment, there is provided a bone joint inserter device as described herein, wherein the width of the first entry port is wider than the first exit port, and the width of the second entry port is wider than the second exit port.

In still another embodiment, there is provided a bone joint inserter device as described herein, wherein the first entry port comprises two holes.

In another embodiment, there is provided a bone joint inserter device as described herein, wherein the second entry port comprises two holes.

In another embodiment, there is provided a bone joint inserter device as described herein, wherein the first entry port comprises two holes, and the second entry port comprises two holes.

In an embodiment, there is provided a bone joint inserter device as described herein, wherein the two holes of the first entry port are arranged in a vertically stacked configuration.

In another embodiment, there is provided a bone joint inserter device as described herein, wherein the two holes of the second entry port are arranged in a vertically stacked configuration.

In a further embodiment, there is provided a bone joint inserter device as described herein, wherein the two holes of the first entry port are arranged in a vertically stacked configuration, and the two holes of the second entry port are arranged in a vertically stacked configuration.

In still another embodiment, there is provided a bone joint inserter device as described herein, wherein the two holes of the first entry port are arranged in a horizontally stacked configuration.

In another embodiment, there is provided a bone joint inserter device as described herein, wherein the two holes of the second entry port are arranged in a horizontally stacked configuration.

In a further embodiment, there is provided a bone joint inserter device as described herein, wherein the two holes of the first entry port are arranged in a horizontally stacked configuration, and the two holes of the second entry port are arranged in a horizontally stacked configuration.

In yet another embodiment, there is provided a bone joint inserter device as described herein, wherein the bone joint is a cervical facet joint.

In another embodiment, there is provided a bone joint inserter device comprising: (a) a proximal section comprising an inserter head, wherein the inserter head comprises: (i) a superior portion comprising a face, wherein the face is configured to engage a bone surface; (ii) an inferior portion comprising at least two prongs, wherein the at least two prongs is configured to engage a bone joint; (iii) a first channel comprising a first entry port and a first exit port, wherein the first entry port is at least as wide as the first exit port, and wherein the first channel is oriented at an acute angle relative to the center line of the inserter head; (iv) a second channel comprising a second entry port and a second exit port, wherein the second entry port is at least as wide as the second exit port, and wherein the second channel is oriented at an acute angle relative to the center line of the inserter head; and (v) a center channel comprising a central entry port and a central exit port, wherein the central entry port is at least as wide as the central exit port, and wherein the center channel is disposed between the first channel and the second channel; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In still another embodiment, there is provided a bone joint inserter device as described herein, wherein the proximal section is fixedly interconnected to the shaft, and the shaft is fixedly interconnected to the distal section.

In yet another embodiment, there is provided a bone joint inserter device as described herein, wherein the proximal section is fixedly interconnected to the shaft, and the shaft is removably interconnected to the distal section.

In another embodiment, there is provided a bone joint inserter device as described herein, wherein the proximal section is removably interconnected to the shaft, and the shaft is fixedly interconnected to the distal section.

In another embodiment, there is provided a bone joint inserter device as described herein, wherein the proximal section is removably interconnected to the shaft, and the shaft is removably interconnected to the distal section.

In still another embodiment, there is provided a bone joint inserter device as described herein, wherein the face is oriented perpendicular to the at least one prong.

In another embodiment, there is provided a bone joint inserter device as described herein, wherein the face is oriented at an acute angle relative to the at least one prong.

In an embodiment, there is provided a bone joint inserter device as described herein, wherein the face is oriented at an obtuse angle relative to the at least one prong.

In an embodiment, there is provided a bone joint inserter device as described herein, wherein the face comprises a surface texture selected from smooth, rough, irregular, knurled, stippled, toothed, and any combination thereof.

In another embodiment, there is provided a bone joint inserter device as described herein, wherein the face comprises a contact surface shape selected from flat, angled, curved, concave, convex, and a combination thereof.

In still another embodiment, there is provided a bone joint inserter device as described herein, wherein the at least two prongs extend from an inferior portion of the face.

In another embodiment, there is provided a bone joint inserter device as described herein, wherein the at least two prongs extend from a superior portion of the face.

In yet another embodiment, there is provided a bone joint inserter device as described herein, wherein the at least two prongs extend from a midline portion of the face.

In an embodiment, there is provided a bone joint inserter device as described herein, wherein each of the at least two prongs independently comprises an end shape selected from pointed, tapered, beveled, chiseled, blunt, rounded, and square.

In another embodiment, there is provided a bone joint inserter device as described herein, wherein the at least two prongs comprise a surface texture selected from smooth, corrugated, stippled, and knurled.

In a further embodiment, there is provided a bone joint inserter device as described herein, wherein the surface texture is present on: the upper surface of the at least two prongs; the lower surface of the at least two prongs; or both the upper surface and lower surface of the at least two prongs.

In yet another embodiment, there is provided a bone joint inserter device as described herein, wherein the shaft comprises a textured surface selected from knurled, corrugated, stippled, and any combination thereof.

In still another embodiment, there is provided a bone joint inserter device as described herein, wherein the shaft comprises an ergonomic grip.

In a further embodiment, there is provided a bone joint inserter device as described herein, wherein the distal portion comprises a notch for orienting a compatible device substantially parallel to the center line of the long axis of the inserter device In another embodiment, there is provided a bone joint inserter device as described herein, wherein the distal section comprises a lumen entry port shape selected from round, rectangular, square, and elliptical.

In yet another embodiment, there is provided a bone joint inserter device as described herein, wherein the first entry port is a slot.

In an embodiment, there is provided a bone joint inserter device as described herein, wherein the second entry port is a slot.

In another embodiment, there is provided a bone joint inserter device as described herein, wherein the first entry port and the second entry port are both a slot.

In still another embodiment, there is provided a bone joint inserter device as described herein, wherein the width of the first entry port is wider than the first exit port.

In another embodiment, there is provided a bone joint inserter device as described herein, wherein the width of the second entry port is wider than the second exit port.

In another embodiment, there is provided a bone joint inserter device as described herein, wherein the width of the first entry port is wider than the first exit port, and the width of the second entry port is wider than the second exit port.

In a further embodiment, there is provided a bone joint inserter device as described herein, wherein the first entry port comprises two holes.

In another embodiment, there is provided a bone joint inserter device as described herein, wherein the second entry port comprises two holes.

In still another embodiment, there is provided a bone joint inserter device as described herein, wherein the first entry port comprises two holes, and the second entry port comprises two holes.

In an embodiment, there is provided a bone joint inserter device as described herein, wherein the two holes of the first entry port are arranged in a vertically stacked configuration.

In another embodiment, there is provided a bone joint inserter device as described herein, wherein the two holes of the second entry port are arranged in a vertically stacked configuration.

In yet another embodiment, there is provided a bone joint inserter device as described herein, wherein the two holes of the first entry port are arranged in a vertically stacked configuration, and the two holes of the second entry port are arranged in a vertically stacked configuration.

In still another embodiment, there is provided a bone joint inserter device as described herein, wherein the two holes of the first entry port are arranged in a horizontally stacked configuration.

In a further embodiment, there is provided a bone joint inserter device as described herein, wherein the two holes of the second entry port are arranged in a horizontally stacked configuration.

In another embodiment, there is provided a bone joint inserter device as described herein, wherein the two holes of the first entry port are arranged in a horizontally stacked configuration, and the two holes of the second entry port are arranged in a horizontally stacked configuration.

In still another embodiment, there is provided a bone joint inserter device according to any one of claims, wherein the bone joint is a cervical facet joint.

In an embodiment, there is provided a cervical facet joint inserter device comprising: (a) a proximal section comprising an inserter head, wherein the inserter head comprises: (i) a superior portion comprising a face, wherein the face is configured to engage a bone surface; (ii) an inferior portion comprising at least two prongs, wherein the at least two prongs is configured to engage a bone joint; (iii) a first channel comprising a first entry port and a first exit port, wherein the first entry port is at least as wide as the first exit port, and wherein the first channel is oriented at an angle ranging from 20 to 45° relative to the center line of the inserter head; (iv) a second channel comprising a second entry port and a second exit port, wherein the second entry port is at least as wide as the second exit port, and wherein the second channel is oriented at an angle ranging from 20 to 45° relative to the center line of the inserter head; and (v) a center channel comprising a central entry port and a central exit port, wherein the central entry port is at least as wide as the central exit port, and wherein the center channel is disposed between the first channel and the second channel; wherein the first channel and the second channel are laterally oriented at opposite angles relative to the center line of the inserter head; (b) a distal section; (c) a shaft disposed between the proximal section and the distal section; and (d) a lumen extending along the central axis from the distal section through the shaft and through the proximal section.

In another embodiment, there is provided a cervical facet joint inserter device as described herein, wherein the proximal section is fixedly interconnected to the shaft, and the shaft is fixedly interconnected to the distal section.

In yet another embodiment, there is provided a cervical facet joint inserter device as described herein, wherein the proximal section is fixedly interconnected to the shaft, and the shaft is removably interconnected to the distal section.

In another embodiment, there is provided a cervical facet joint inserter device as described herein, wherein the proximal section is removably interconnected to the shaft, and the shaft is fixedly interconnected to the distal section.

In another embodiment, there is provided a cervical facet joint inserter device as described herein, wherein the proximal section is removably interconnected to the shaft, and the shaft is removably interconnected to the distal section.

In another embodiment, there is provided a cervical facet joint inserter device as described herein, wherein the face is oriented perpendicular to the at least one prong.

In another embodiment, there is provided a cervical facet joint inserter device as described herein, wherein the face is oriented at an acute angle relative to the at least one prong.

In still another embodiment, there is provided a cervical facet joint inserter device as described herein, wherein the face is oriented at an obtuse angle relative to the at least one prong.

In another embodiment, there is provided a cervical facet joint inserter device as described herein, wherein the face comprises a surface texture selected from smooth, rough, irregular, knurled, stippled, toothed, and any combination thereof.

In another embodiment, there is provided a cervical facet joint inserter device as described herein, wherein the face comprises a contact surface shape selected from flat, angled, curved, concave, convex, and a combination thereof.

In a further embodiment, there is provided a cervical facet joint inserter device as described herein, wherein the at least two prongs extend from an inferior portion of the face.

In yet another embodiment, there is provided a cervical facet joint inserter device as described herein, wherein the at least two prongs extend from a superior portion of the face.

In another embodiment, there is provided a cervical facet joint inserter device as described herein, wherein the at least two prongs extend from a midline portion of the face.

In still another embodiment, there is provided a cervical facet joint inserter device as described herein, wherein the at least two prongs comprise an end shape selected from pointed, tapered, beveled, chiseled, blunt, rounded, and square.

In an embodiment, there is provided a cervical facet joint inserter device as described herein, wherein the at least two prongs comprise a surface texture selected from smooth, corrugated, stippled, and knurled.

In another embodiment, there is provided a cervical facet joint inserter device as described herein, wherein the surface texture is present on: the upper surface of the at least one prong; the lower surface of the at least one prong; or both the upper surface and lower surface of the at least one prong.

In yet another embodiment, there is provided a cervical facet joint inserter device as described herein, wherein the shaft comprises a textured surface selected from knurled, corrugated, stippled, and any combination thereof.

In another embodiment, there is provided a cervical facet joint inserter device as described herein, wherein the shaft comprises an ergonomic grip.

In still another embodiment, there is provided a cervical facet joint inserter device as described herein, wherein the distal portion comprises a notch for orienting a compatible device substantially parallel to the center line of the long axis of the inserter device In an embodiment, there is provided a cervical facet joint inserter device as described herein, wherein the distal section comprises a lumen entry port shape selected from round, rectangular, square, and elliptical.

In another embodiment, there is provided a cervical facet joint inserter device as described herein, wherein the first entry port is a slot.

In a further embodiment, there is provided a cervical facet joint inserter device as described herein, wherein the second entry port is a slot.

In another embodiment, there is provided a cervical facet joint inserter device as described herein, wherein the first entry port and the second entry port are both a slot.

In still another embodiment, there is provided a cervical facet joint inserter device as described herein, wherein the width of the first entry port is wider than the first exit port.

In another embodiment, there is provided a cervical facet joint inserter device as described herein, wherein the width of the second entry port is wider than the second exit port.

In an embodiment, there is provided a cervical facet joint inserter device as described herein, wherein the width of the first entry port is wider than the first exit port, and the width of the second entry port is wider than the second exit port.

In a further embodiment, there is provided a cervical facet joint inserter device as described herein, wherein the first entry port comprises two holes.

In yet another embodiment, there is provided a cervical facet joint inserter device as described herein, wherein the second entry port comprises two holes.

In still another embodiment, there is provided a cervical facet joint inserter device as described herein, wherein the first entry port comprises two holes, and the second entry port comprises two holes.

In yet another embodiment, there is provided a cervical facet joint inserter device as described herein, wherein the two holes of the first entry port are arranged in a vertically stacked configuration.

In another embodiment, there is provided a cervical facet joint inserter device as described herein, wherein the two holes of the second entry port are arranged in a vertically stacked configuration.

In still another embodiment, there is provided a cervical facet joint inserter device as described herein, wherein the two holes of the first entry port are arranged in a vertically stacked configuration, and the two holes of the second entry port are arranged in a vertically stacked configuration.

In an embodiment, there is provided a cervical facet joint inserter device as described herein, wherein the two holes of the first entry port are arranged in a horizontally stacked configuration.

In another embodiment, there is provided a cervical facet joint inserter device as described herein, wherein the two holes of the second entry port are arranged in a horizontally stacked configuration.

In yet another embodiment, there is provided a cervical facet joint inserter device as described herein, wherein the two holes of the first entry port are arranged in a horizontally stacked configuration, and the two holes of the second entry port are arranged in a horizontally stacked configuration.

In another embodiment, there is provided a cervical facet joint inserter kit comprising: (a) a cervical facet joint inserter device comprising: (i) a proximal section comprising an inserter head, wherein the inserter head comprises: (aa) a superior portion comprising a face, wherein the face is configured to engage a bone surface; (bb) an inferior portion comprising at least two prongs, wherein the at least two prongs is configured to engage a bone joint; (cc) a first channel comprising a first entry port and a first exit port, wherein the first entry port is at least as wide as the first exit port, and wherein the first channel is oriented at an angle ranging from 20 to 45° relative to the center line of the inserter head; (dd) a second channel comprising a second entry port and a second exit port, wherein the second entry port is at least as wide as the second exit port, and wherein the second channel is oriented at an angle ranging from 20 to 45° relative to the center line of the inserter head; and (ee) a center channel comprising a central entry port and a central exit port, wherein the central entry port is at least as wide as the central exit port, and wherein the center channel is disposed between the first channel and the second channel; wherein the first channel and the second channel are laterally oriented at opposite angles relative to the center line of the inserter head; (ii) a distal section; (iii) a shaft disposed between the proximal section and the distal section; and (iv) a lumen extending along the central axis from the distal section through the shaft and through the proximal section; (b) a cutting instrument selected from a drill bit, a stylet, a rasp, a burr, or a combination thereof; and (c) a printed set of instructions.

In an embodiment, there is provided a method for inserting a bone anchor device into a lateral mass adjacent to a cervical facet joint, the method comprising: (a) providing a bone anchor inserter device comprising: (i) a proximal section comprising an inserter head, wherein the inserter head comprises: (aa) a superior portion comprising a face, wherein the face is configured to engage a bone surface; (bb) an inferior portion comprising at least two prongs, wherein the at least two prongs is configured to engage a bone joint; (cc) a first channel comprising a first entry port and a first exit port, wherein the first entry port is at least as wide as the first exit port, and wherein the first channel is oriented at an angle ranging from 20 to 45° relative to the center line of the inserter head; (dd) a second channel comprising a second entry port and a second exit port, wherein the second entry port is at least as wide as the second exit port, and wherein the second channel is oriented at an angle ranging from 20 to 45° relative to the center line of the inserter head; and (ee) a center channel comprising a central entry port and a central exit port, wherein the central entry port is at least as wide as the central exit port, and wherein the center channel is disposed between the first channel and the second channel; wherein the first channel and the second channel are laterally oriented at opposite angles relative to the center line of the inserter head; (ii) a distal section; (iii) a shaft disposed between the proximal section and the distal section; and (iv) a lumen extending along the central axis from the distal section through the shaft and through the proximal section; (b) creating an access opening to expose a target cervical facet joint; (c) inserting the at least two prongs of the inserter head into the target cervical facet joint; (d) aligning the face of the inserter head with the target bone surface; (e) introducing a cutting instrument through at least one of the first channel and the second channel; (f) impacting the target bone surface with the cutting instrument to produce a receiving site for the bone anchor device; (g) disengaging the cutting instrument from the target bone surface; (h) withdrawing the bone anchor inserter device; and (i) inserting the bone anchor device into the receiving site on the target bone.

In another embodiment, there is provided a method for inserting a bone anchor device into a lateral mass adjacent to a cervical facet joint, the method comprising: (a) providing a bone anchor inserter device comprising: (i) a proximal section comprising an inserter head, wherein said inserter head comprises: (aa) a superior portion comprising a face, wherein said face is configured to engage a bone surface; (bb) an inferior portion comprising at least two prongs, wherein said at least two prongs is configured to engage a bone joint; (cc) a first channel comprising a first entry port and a first exit port, wherein said first entry port is at least as wide as said first exit port, and wherein said first channel is oriented at an angle ranging from 20 to 45° relative to the center line of said inserter head; (dd) a second channel comprising a second entry port and a second exit port, wherein said second entry port is at least as wide as said second exit port, and wherein said second channel is oriented at an angle ranging from 20 to 45° relative to the center line of said inserter head; and (ee) a center channel comprising a central entry port and a central exit port, wherein said central entry port is at least as wide as said central exit port, and wherein said center channel is disposed between said first channel and said second channel; wherein said first channel and said second channel are laterally oriented at opposite angles relative to the center line of said inserter head; (ii) a distal section; (iii) a shaft disposed between said proximal section and said distal section; and (iv) a lumen extending along the central axis from said distal section through said shaft and through said proximal section; (b) creating an access opening to expose a target cervical facet joint; (c) inserting said at least two prongs of said inserter head into the target cervical facet joint; (d) aligning said face of said inserter head with the target bone surface; (e) introducing a cutting instrument through at least one of said central channel, said first channel and said second channel; (f) impacting the target bone surface with said cutting instrument to produce a receiving site for said bone anchor device; (g) disengaging said cutting instrument from said target bone surface; (h) withdrawing the bone anchor inserter device; and (i) inserting the bone anchor device into the receiving site on the target bone.

In a further embodiment, there is provided a method for inserting a bone anchor device into a lateral mass adjacent to a cervical facet joint, the method comprising: (a) providing a bone anchor inserter device comprising: (i) a proximal section comprising an inserter head, wherein said inserter head comprises: (aa) a superior portion comprising a face, wherein said face is configured to engage a bone surface; (bb) an inferior portion comprising at least two prongs, wherein said at least two prongs is configured to engage a bone joint; (cc) a first channel comprising a first entry port and a first exit port, wherein said first entry port is at least as wide as said first exit port, and wherein said first channel is oriented at an angle ranging from 20 to 45° relative to the center line of said inserter head; (dd) a second channel comprising a second entry port and a second exit port, wherein said second entry port is at least as wide as said second exit port, and wherein said second channel is oriented at an angle ranging from 20 to 45° relative to the center line of said inserter head; and (ee) a center channel comprising a central entry port and a central exit port, wherein said central entry port is at least as wide as said central exit port, and wherein said center channel is disposed between said first channel and said second channel; wherein said first channel and said second channel are laterally oriented at opposite angles relative to the center line of said inserter head; (ii) a distal section; (iii)

a shaft disposed between said proximal section and said
      distal section; and (iv)
   a lumen extending along the central axis from said distal
      section through said shaft and through said proximal
      section; (b) creating an access opening to expose a
      target cervical facet joint; (c) inserting said at least two
      prongs of said inserter head into the target cervical facet
      joint; (d) aligning said face of said inserter head with
      the target bone surface; (e) introducing a cutting instru-
      ment through said central channel; (f) impacting the
      target bone surface with said cutting instrument to
      produce a receiving site for said bone anchor device;
      (g) disengaging said cutting instrument from said target
      bone surface; (h) withdrawing the bone anchor inserter
      device; and (i) inserting the bone anchor device into the
      receiving site on the target bone.

In any of the methods described herein and/or in the claims, any combination of the recited steps can occur and in any order, based on surgeon preference and the applicable approach due to individual patient characteristics and surgical needs.

BRIEF DESCRIPTION OF THE FIGURES

FIG. 1 is a perspective view of an example bone joint inserter device.

FIG. 2 is a distal end view of an example bone joint inserter device.

FIG. 7a is a perspective view of an alternative example of a bone joint inserter device.

FIG. 7b is a distal view of an alternative example of a bone joint inserter device.

FIG. 7c provides alternative embodiments of lumen entry ports of a bone joint inserter device.

FIG. 9 provides a perspective view of an example bone joint inserter device, demonstrating a drill bit residing in an upper hole of a channel and extending from an upper exit port, and alternatively demonstrating a drill bit residing in a lower hole of a channel and extending from a lower exit port.

DETAILED DESCRIPTION

Figure 3A:
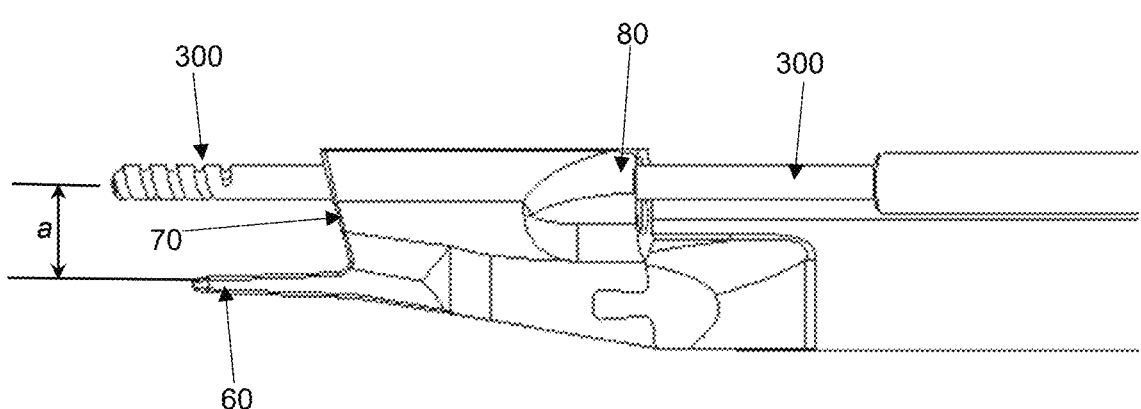
FIG. 3a is a closeup transparent side view of an example bone joint inserter device, showing a drill bit inserted through a channel in the inserter head.

The following detailed description provides further disclosure with reference to the accompanying drawings.

Certain exemplary embodiments ("examples", "embodiments", etc.) are described to provide an overall understanding of the principles of the function, structure, manufacture, use and preparation of the devices and methodology disclosed herein. While one or more embodiments and/or examples are described and illustrated in the accompanying drawings, one of skill in the relevant art will readily understand that the devices, processes, methods of use, relevant drawings, and the like specifically described herein are non-limiting exemplary embodiments and that the scope of the invention is defined by the accompanying claims in this disclosure. The features described, illustrated or exemplified with one or more embodiments may also be combined with the features of one or more other examples or embodiments. Such combinations, modifications, and variations are included within the scope of the presently described invention. One of ordinary skill in the art will appreciate and readily understand that the devices disclosed herein can have various configurations in addition to the examples and embodiments disclosed herein, and that the various features as disclosed herein in the various embodiments are interchangeable and able to be combined.

In general, various instruments are provided for accessing bone joints, including, for example, cervical facet joints, creating a repeatable defect within the facet joint, providing a guide for the placement of bone anchors into the lateral bone mass, and optionally deploying bone graft into the defect to promote fusion. Use of these instruments can provide a repeatable method for both preparing the bone joint and placing one or more bone anchors, to improve surgical accuracy and thus patient safety. The instruments generally include an inserter device, a tamp, a cutting tool (also referred to as a cutting bit) and a lateral mass stylet. All instruments are configured to be used together such that they provide a repeatable and efficient surgical workflow for improved patient safety when performing posterior cervical fusion procedures. Along with cervical facet joints, the insertion device can also be employed in accessing a joint between many types of bone, including, for example, a knee, elbow, ankle, shoulder, hip, or other spinal joint(s) of a human or any other animal.

Throughout this description, the term "inserter face" is synonymous with "face", and "inserter head" is synonymous with "head".

Figure 1:
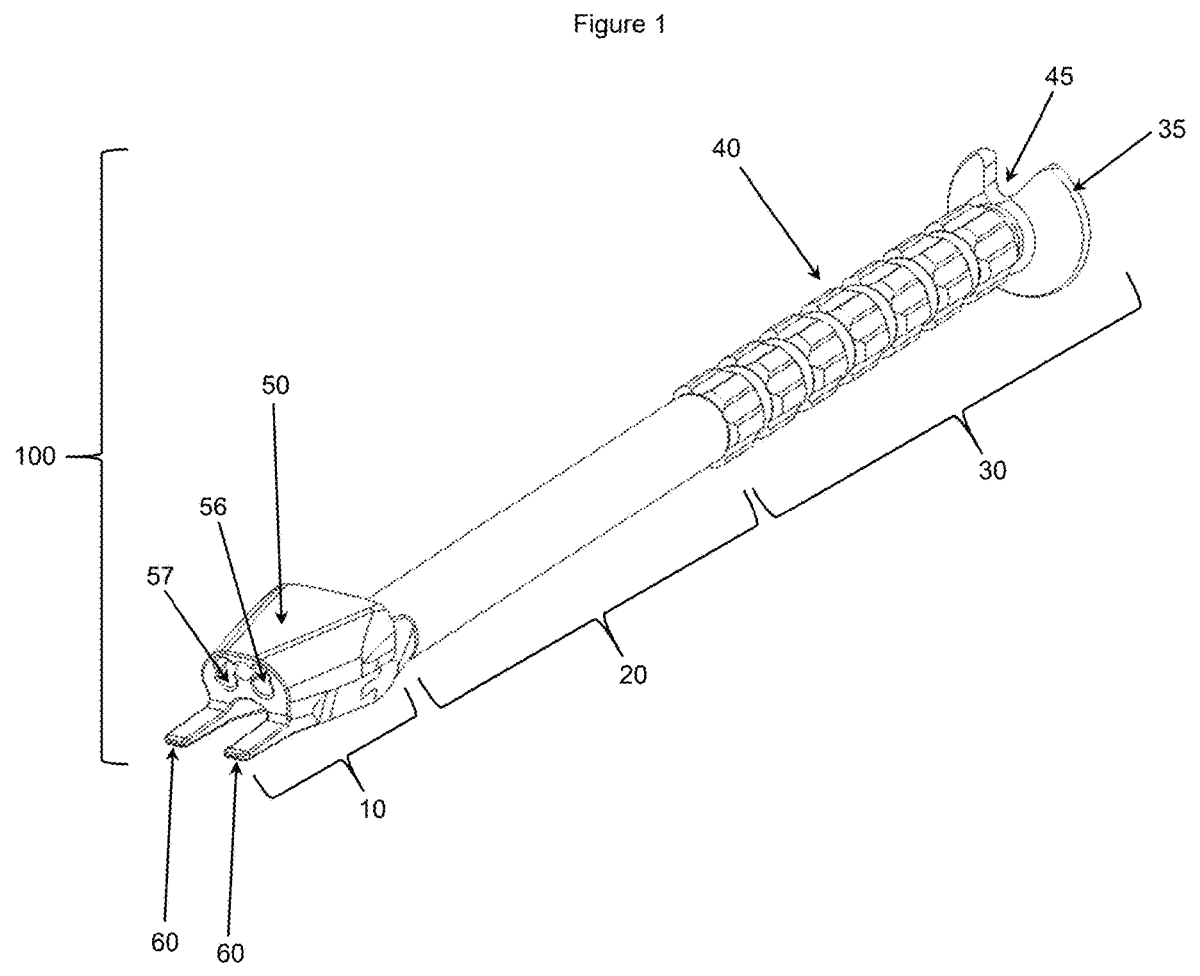

In an embodiment exemplified in FIG. 1, inserter device (100) includes a longitudinal shaft (20) with a proximal section (10) and distal section (30), and a lumen (25; not shown) extending through the length of the inserter device (100). At the proximal end of the inserter device (100) is the inserter head (50) which is configured to engage the cervical facet joint. The shaft (20) generally extends longitudinally from the inserter head (50) toward the distal end of the inserter device (100). In an embodiment, shaft (20) is configured with a textured surface that can also be shaped to allow the user to grip the instrument. Without being limited by this example, this grip section of shaft (20) can have a different patterned texture, such as ridges, knurling, a stippled pattern of regular or irregular protrusions, a cross-hatched surface, and the like, and may also be ergonomically shaped for comfort in handling and controlling the inserter device (100). The grip (40) of shaft (20) may also be made of various materials, including a metal or metal alloy, a plastic or plastic-derivative material, rubber, silicon, and any material able to withstand sterilization (including autoclaving, or any other conventional sterilization process), or any combination thereof. One of skill in the art will also readily understand that any appropriate material for making surgical instruments also applies to the present invention.

In one or more embodiments, proximal section (10), distal section (30), and shaft (20) of inserter device (100) all can be integrated as a single unit, can be modular components, or a combination of modular components and fixed components. For example, inserter head (50) of different channel and/or prong (60) configurations may be exchanged with minimal effort in order to customize the inserter device (100) for use with varying patient anatomical variations and surgeon preferences. In another example, a modular shaft (20) of varying configurations, including various diameters, various lumen (25) configurations (including round, elliptical, or oval lumen (25) configurations) and/or lengths, can also be removably or permanently attached with proximal and distal sections (10 and 30, respectively) of the inserter device (100). In a further example, distal section (30) can be a removable or fixed section including a funnel for introducing material through the inserter device (100), and/or the distal section (30) can provide an impaction surface for engaging a hammer or mallet to drive the inserter device (100) into a facet joint and/or into another anatomical region. Further, modularity of entry point or exit port of lumen (25) in one or more embodiments facilitates the use of different cutting tools, drill bits, taps, tamps, and the like. For example, in operating the inserter device (100), the user can minimize or eliminate the need to fully withdraw a drill bit or other cutting device to move to an alternative exit port by slightly withdrawing drill bit from exit port back into the relevant channel, then reinserting the drill bit into an alternative entry port and out through the corresponding exit port to provide an appropriately sized guide housing and desired trajectory for the drill bit.

In one or more embodiments, distal section (30) having a lumen (25) can be exchanged for a different lumen (25) configuration so as to facilitate use of different cutting tool or tamp configurations. Also, distal section (30) having a lumen (25) of any configuration can be exchanged for a distal section (30) having no lumen (25) (i.e., is a solid, honeycombed or other rigid structure) for use with a mallet or surgical hammer in orienting prong (60) location and/or driving prong (60) (s) or other attached device, such as a cutting blade or stylet, into a bone joint or other anatomical region.

In one or more embodiments, inserter device (100) configurations as described herein are compatible with various secondary device attachments, such as different guides employed for placement and/or insertion of bone anchor devices, including bone screws of various sizes and configurations.

In an embodiment as illustrated in FIG. 1, distal end of inserter device (100) has a modular or integrated conical shaped distal end (35) similar to a funnel surrounding distal entry to lumen (25) to facilitate introduction of various materials into and through the hollow tube of the lumen (25). For example, a user can introduce a biomaterial in various formulations or configurations, including a bioerodible or bioresorbable material, demineralized bone material (DBM), demineralized bone fibers (DBF) granules, a slurry, a paste, a plaster, a putty, a plug, a bone cement, a liquid formulation, a solid formulation, a semi-solid formulation, or a powder formulation, a granular formulation, a binder, a polymeric material, one or more therapeutic component(s), and the like, including any combination of these or other materials. Introduction of these or other materials into the lumen (25) affords the user convenience and speed in introducing material through the inserter device (100) and into a corresponding receiving hole in the target bone or joint section. In an embodiment, the example conical shaped distal end (35) can also provide a notch (45) for engaging one or more separate components for use with the inserter device (100). In such an embodiment, notch (45) may be oriented to accommodate different tool configurations such as an extended cutting bit, stylet, tamp, and the like.

Further in FIG. 1, there is provided an example of an inserter head (50) with a first exit port (56) and a second exit port (57). These first and second exit ports (56 and 57, respectively) are shown in an example of their placement in the inserter face (70) of the inserter head (50). Also, an example of two prongs (60) on the proximal end are shown. In this example, prongs (6) are illustrated having a beveled tip on the proximal end of each prong (60). Further, distal section (30) illustrates an example of a grip (40) for ease of user manipulation and control of inserter device (100).

In another embodiment exemplified in FIG. 2, there is provided a distal view of inserter device (100). In this embodiment, round lumen entry port (150) is shown, along with lumen (25), notch (45) and grip (40). Shaft (20) is connected to inserter head (50), and inserter head (50) further contains a first channel (58) with a first entry port (54), a center channel (51), and a second channel (59) with a second entry port (55). Both of first entry port (54) and second entry port (55) in this representative configuration each employ a double barrel entry port that is also referred to as a vertically stacked port or a FIG. 8 configuration. In an example inserter device containing a funnel that can be used for introduction of material into and through lumen, notch (45) also is configured to allow a drill or other representative device to access the central channel. In this embodiment, notch also acts to guide cutting tool to reside approximately in parallel with shaft (20).

Further, an exemplified embodiment in FIG. 3a illustrates one example of a cutting bit (300) inserted into a superior portion (80) entry port and emerging out through a superior portion (80) exit port. Distance a illustrates the representative distance measured from the emergence of cutting bit (300) to the location of prong (60) extending in a proximal direction from the inferior portion (90) of inserter face (70). Also, inserter face (70) in this example is oriented at an acute angle relative to prong (60).

Figure 3B:
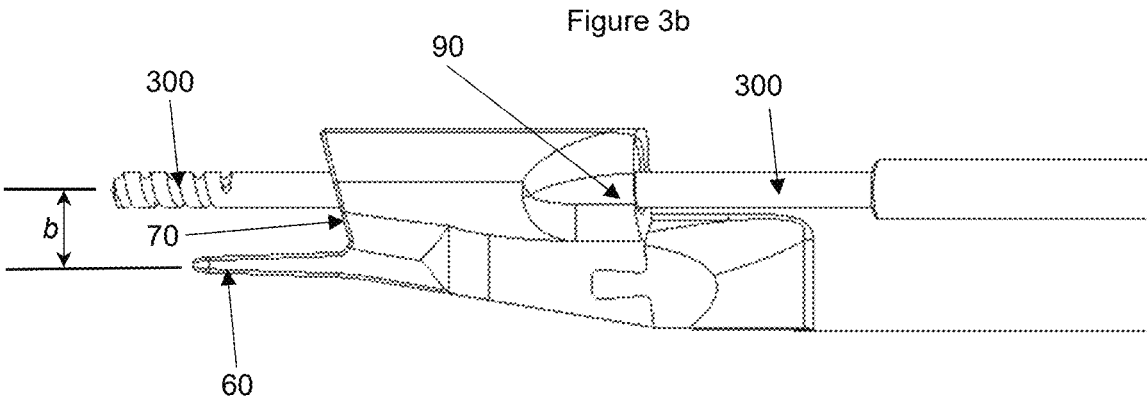
FIG. 3b is a closeup transparent side view of an example bone joint inserter device, showing a drill bit inserted through an alternative channel in the inserter head.

In another example, FIG. 3b illustrates a cutting bit (300) inserted into an inferior portion (90) entry port and emerging out through an inferior portion (90) exit port. Distance b illustrates the representative distance measured from the emergence of cutting bit (300) to the location of prong (60) extending in a proximal direction from the inferior portion (90) of inserter face (70). Also, inserter face (70) in this example is oriented at an acute angle relative to prong (60).

Figure 4:
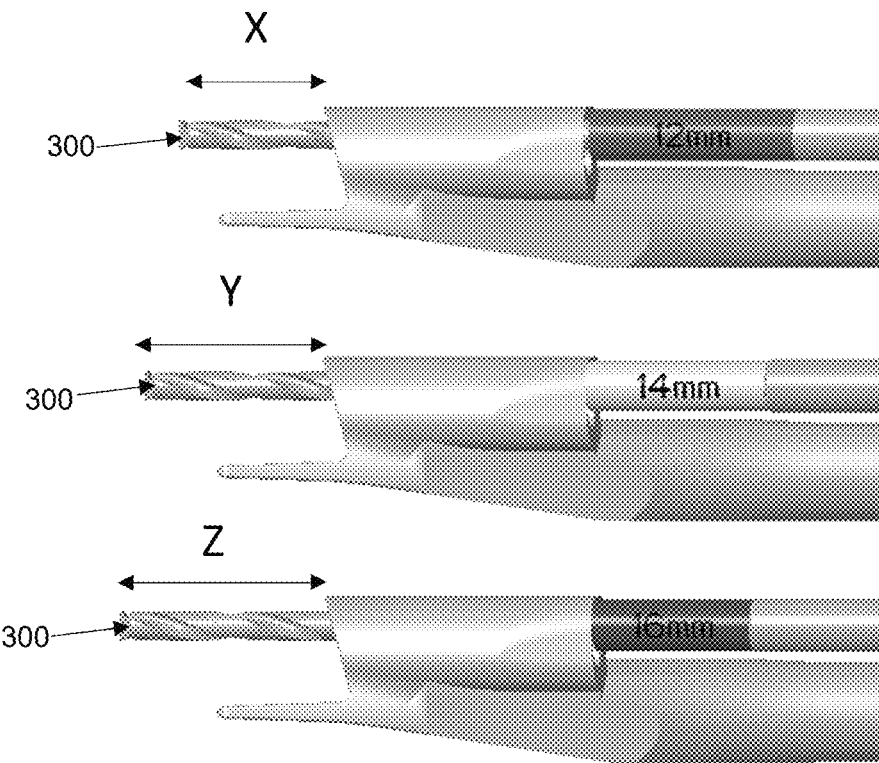
FIG. 4 is a series of closeup side views of an example bone joint inserter device, demonstrating different lengths (X, Y and Z) of drill bit protrusion from a representative inserter head exit port.

FIG. 4 illustrates various embodiments with differing cutting bit (300) lengths emerging from an exit port on inserter face (70). For example, distance X corresponds in this example to a 12 mm cutting bit length; distance Y corresponds in this example to a 14 mm cutting bit length; and distance Z corresponds in this example to a 16 mm cutting bit length. Other cutting bit lengths can be used, and these examples are for illustrative purposes only. One of skill in the art readily understands that a cutting bit length is determined by surgeon preference and/or lateral mass parameters including depth and diameter of cut, and the inserter device (100) accommodates such variations in cutting bit (300) lengths beyond these exemplified lengths that are not intended to limit the cutting bits (300) that can be employed with the inserter device (100).

Figure 5:
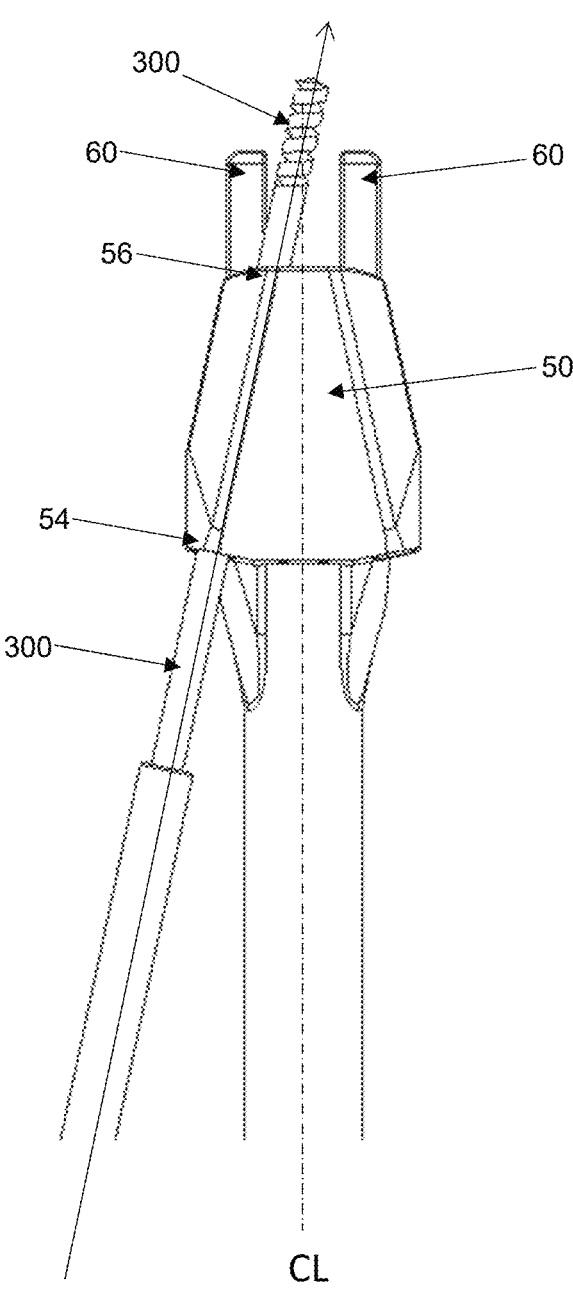
FIG. 5 is a top transparent view of an example bone joint inserter device, demonstrating a drill bit residing in an angled channel relative to a center line (CL).

In an embodiment shown in FIG. 5, an example cutting bit (300) is presented disposed at an angled orientation within a first channel (58) as the cutting bit (300) passes from the first entry port (54) though first channel (58) and out through first exit port (56). Center line (CL) of inserter head (50) is also indicated to illustrate the angular trajectory of cutting bit (300) through inserter head (50).

Figure 6A:
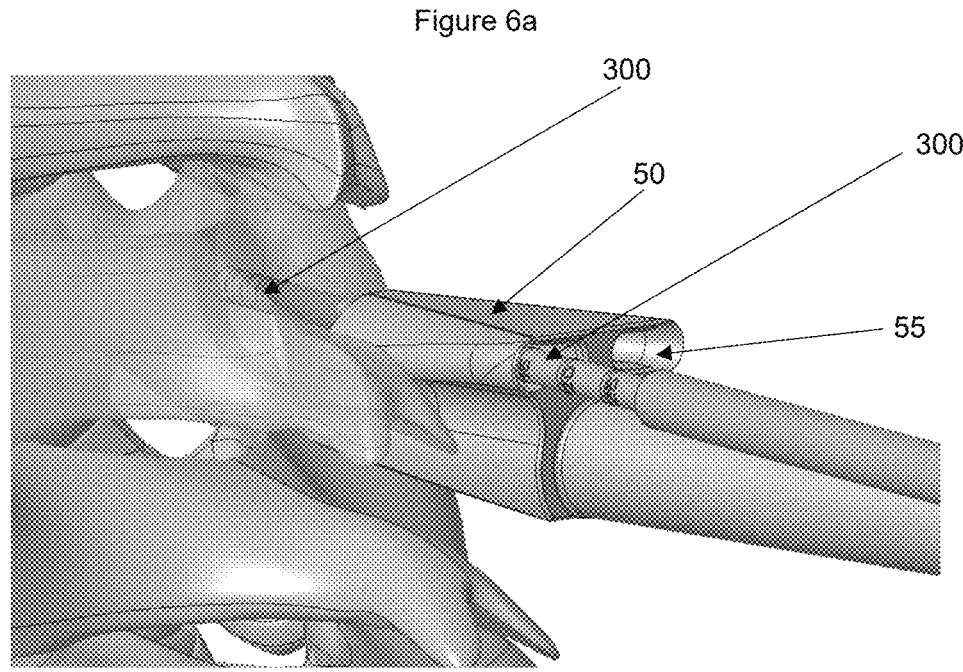
FIG. 6a is a perspective view of an example bone joint inserter device, demonstrating engagement of a bone inserter device with a facet joint, and an example drill bit in a channel slot contacting a lateral mass.
Figure 6B:
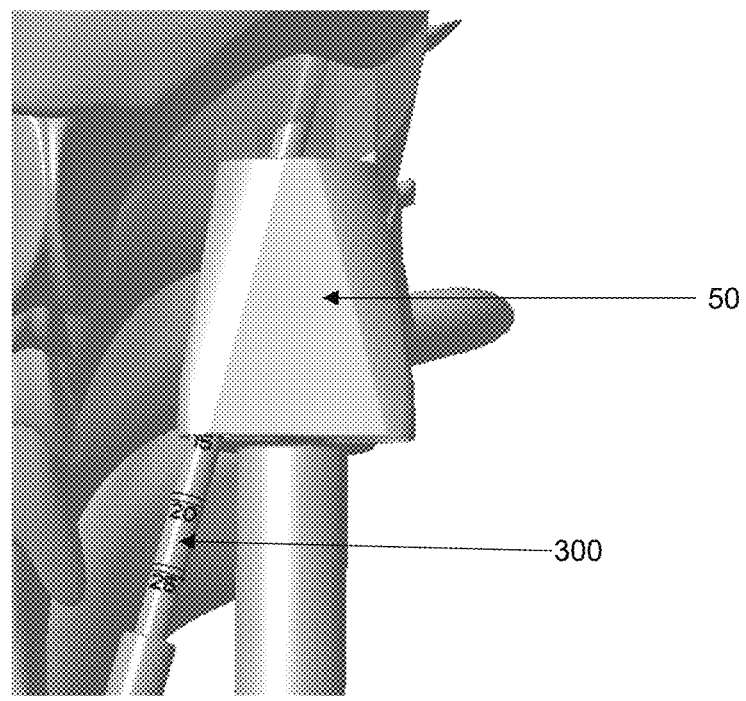
FIG. 6b is a top view of an example bone joint inserter device, demonstrating engagement of a bone inserter device with a facet joint, and an example drill bit in a channel slot contacting a lateral mass.

Also, FIG. 6a illustrates an example of an inserter device (100) engaging a facet joint and the position of cutting bit (300) as the tip of cutting bit (300) engages the target lateral mass. Prongs (60; not shown) engage the facet joint to orient the inserter device (300) for manipulation of the surrounding bone. Cutting bit (300) angularly resides in first entry port (54) at the medial limit of entry port (54). Second entry port (55) is shown for comparison purposes. FIG. 6b illustrates a comparative top view of this example embodiment that further exemplifies placement of cutting bit (300) in an angular trajectory relative to inserter head (50) into and through first entry port (54) to engage the lateral mass.

An embodiment provided in FIG. 7a shows an inserter device (100) configured with 2 prongs (60) disposed in approximately the horizontal midline area of face (70). This embodiment also illustrates a textured grip (40) on distal section (30) of inserter device (100). Prongs (60) are shown having a textured surface located on approximately the middle portion of each prong (60).

FIG. 7b illustrates an embodiment of a horizontally stacked lumen entry port (160) of an inserter device (100). Similarly, FIG. 7c demonstrates a sample of other configurations for a lumen (25) entry: a circular or round lumen entry port (150); a horizontally stacked lumen entry port (160); an elliptical lumen entry port (170) (also referred to as a slot lumen entry port); and a rectangular lumen entry port (180). The example rectangular lumen entry port (180) in particular can accommodate a chisel or other similarly shaped cutting instrument.

Figure 8:
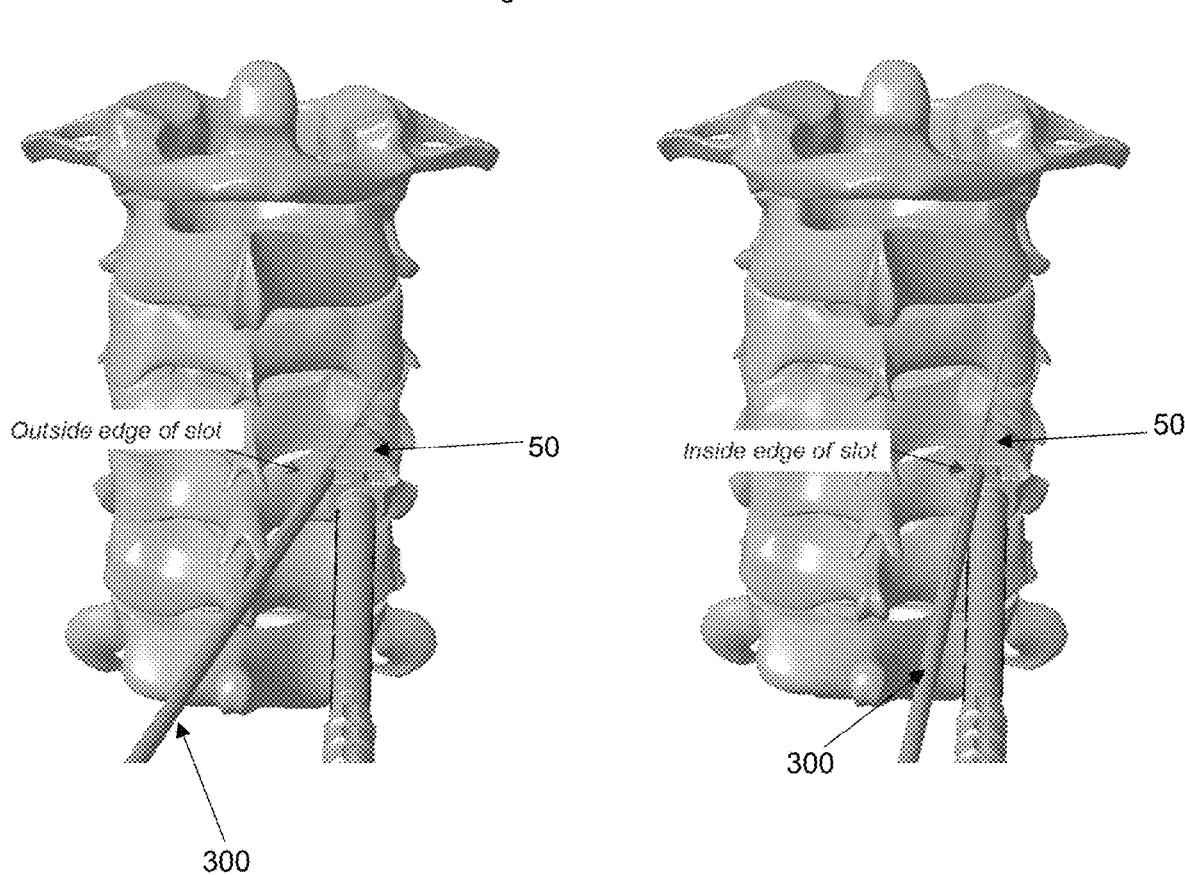
FIG. 8 is a perspective view of an example bone joint inserter device, demonstrating engagement of a bone inserter device with a facet joint, and showing examples of drill bit placement in various positions within an example channel slot at the "outside edge" and "inside edge" of the representative slot.

FIG. 8 illustrates an embodiment of an inserter device (100) in which prongs (60; not shown) engage the facet joint and inserter face (70; not shown) contacts the surrounding bone to limit any further penetration of the inserter device (100) into the facet joint. In the left-hand figure, cutting bit (300) is inserted through the outside edge of the slot (i.e., first entry port (54)), and the trajectory of the cutting bit (300) is at an angle that is greater than if the cutting bit (300) were to engage the inside edge of slot (i.e., first entry port 54), as demonstrated comparatively in the right-hand figure. In use of the inserter device (100), a surgeon can further adjust the angle of trajectory for cutting bit (300) between these two example positions by relocating cutting bit (300) laterally away from the outside edge of slot to reduce the incident angle between the cutting bit (300) and the midline of inserter head (50).

An example embodiment of inserter head (50) shown in FIG. 9 demonstrates disposition of cutting bit (300) emerging from an upper hole of first exit port (56) on face (70), as compared to disposition of cutting bit (300) emerging from a lower hole of first exit port (56) on face (70). Prongs (60) in this embodiment are also shown to illustrate relative location of cutting bit (300). Left-hand figures for both Upper Hole and Lower Hole provide perspective views of inserter head (50), while right-hand figures for both Upper Hole and Lower Hole provide side views of emerging cutting bit (300) for comparison purposes.

Figure 10:
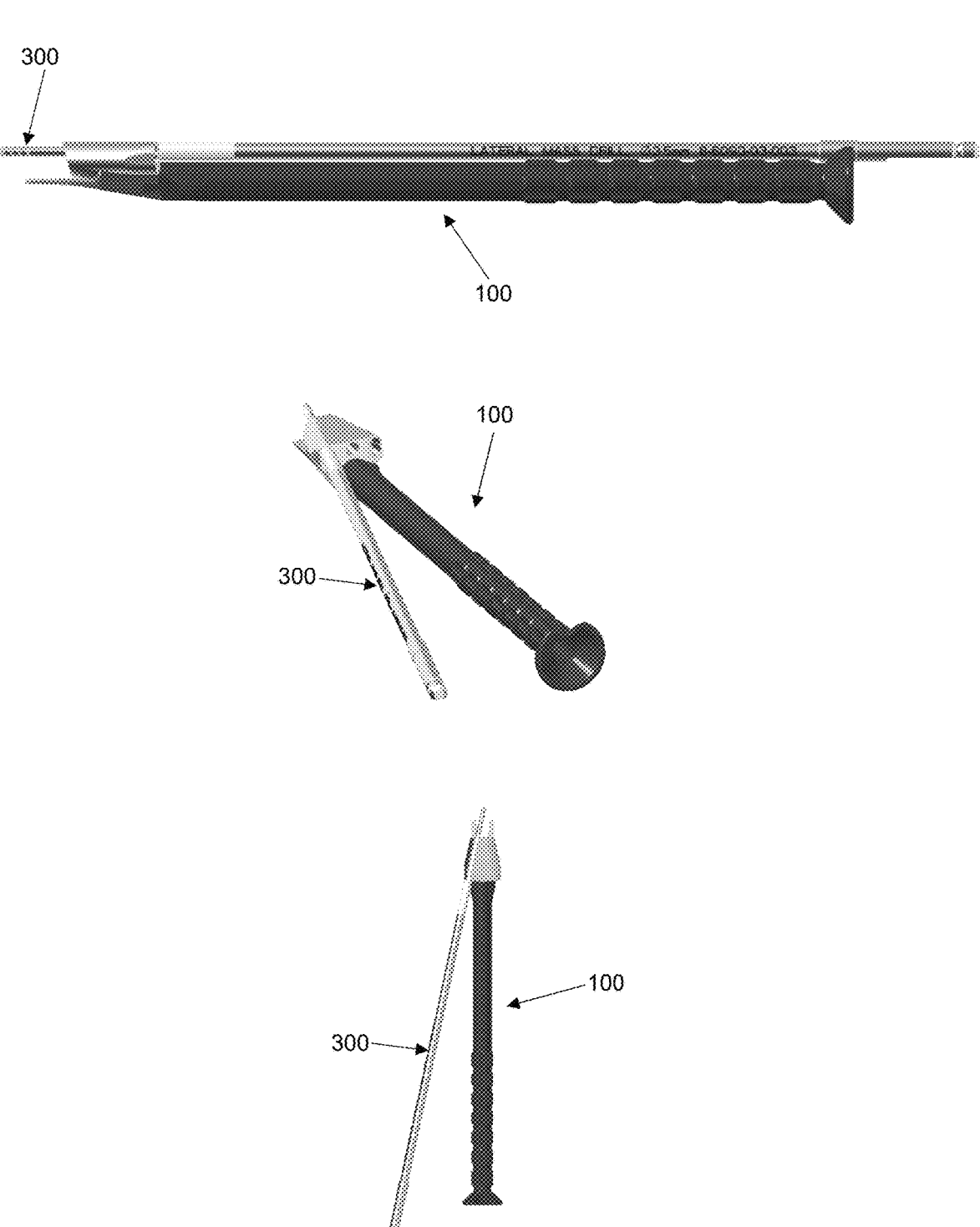
FIG. 10 provides a side view, perspective view, and top view, respectively, of an example bone joint inserter device with a corresponding drill bit engaged with a head inserter channel.

FIG. 10 provides a side view (top image) of an example inserter device (100) with an embodiment housing a cutting bit (300) along the midline of inserter device (300) and aligned within the confines of notch (45) in distal section (30). In this embodiment, cutting bit (300) emerges from center channel (51) on superior portion (80) of face (70; not shown). An alternative embodiment shown in perspective view (center image) demonstrates a cutting bit (300) disposed in a first channel (58; not shown), and again shown from a top view (bottom image).

Figure 11:
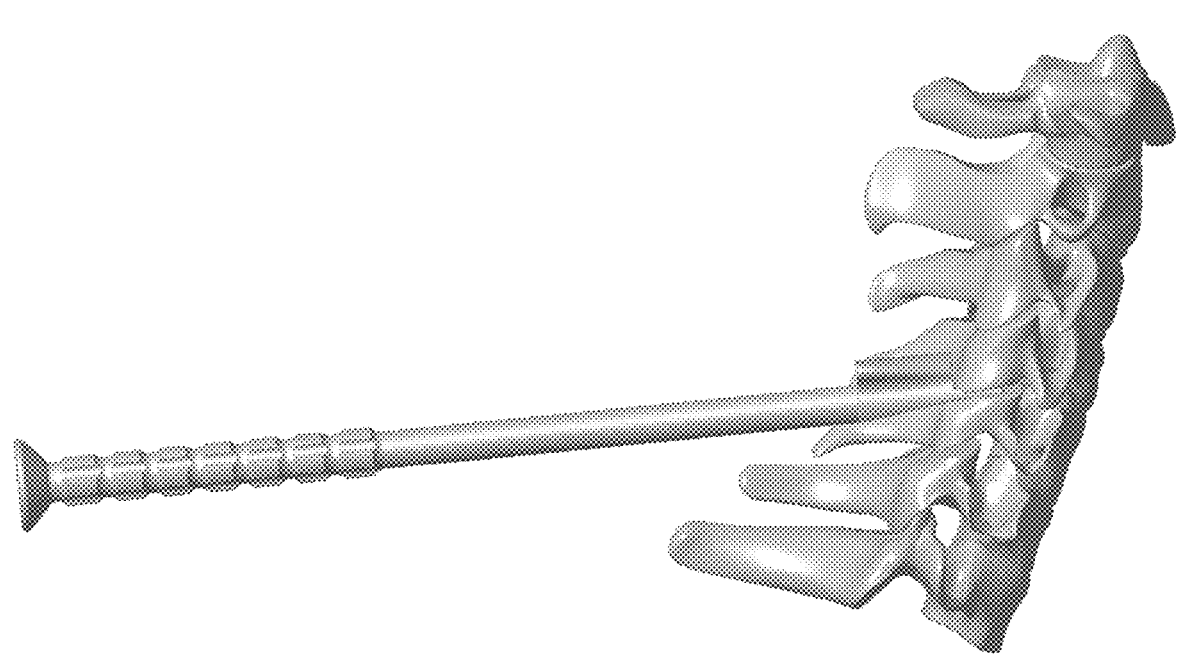
FIG. 11 provides a side perspective view of an example bone joint inserter device engaged with a cervical facet joint.

In an embodiment illustrated in FIG. 11, an example inserter device (300) provides a proximal section (10) with a pair of prongs (60; not shown) disposed in a facet joint and a face (70; not shown) engaged with bone surface surrounding facet joint that limits further penetration of inserter device (300) into facet joint.

Figure 12A:
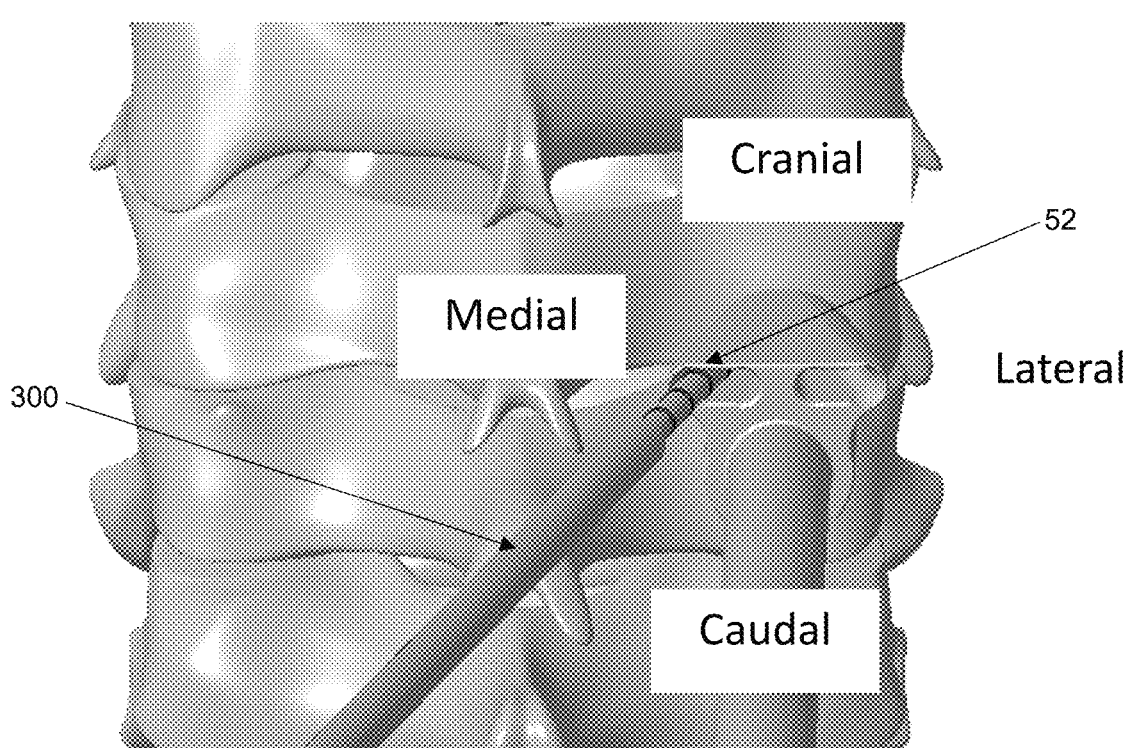
FIG. 12a is a perspective view of an example bone joint inserter device engaged with a cervical facet joint, demonstrating a drill bit housed in a channel slot and directed from medial to lateral direction to engage the lateral mass.
Figure 12B:
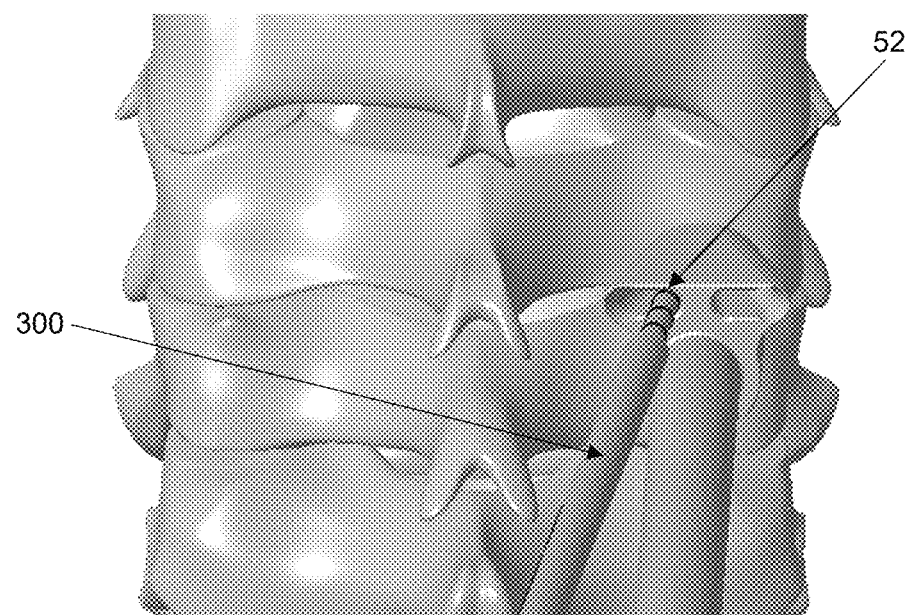
FIG. 12b is an alternative perspective view of an example bone joint inserter device engaged with a cervical facet joint, demonstrating a drill bit housed in a channel slot and directed from medial to lateral direction to engage the lateral mass.

FIGS. 12a and 12b illustrate another embodiment of an inserter device (100) similar to FIG. 8, but with enhanced detail showing partial insertion of cutting bit (300) into the outside edge of a first lateral slot (52) (see FIG. 12a), compared with partial insertion of cutting bit (300) into the inside edge of first lateral slot (52) (see FIG. 12b).

Figure 13A:
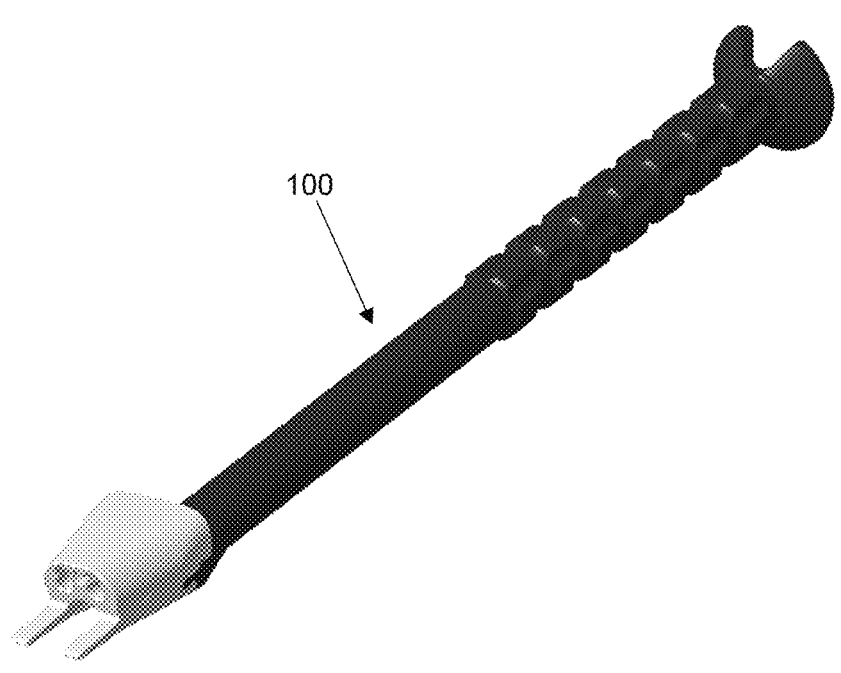
FIG. 13a is a perspective view of an example bone joint inserter device, demonstrating an embodiment with a notch in the distal section for compatibility with various instruments.
Figure 13B:
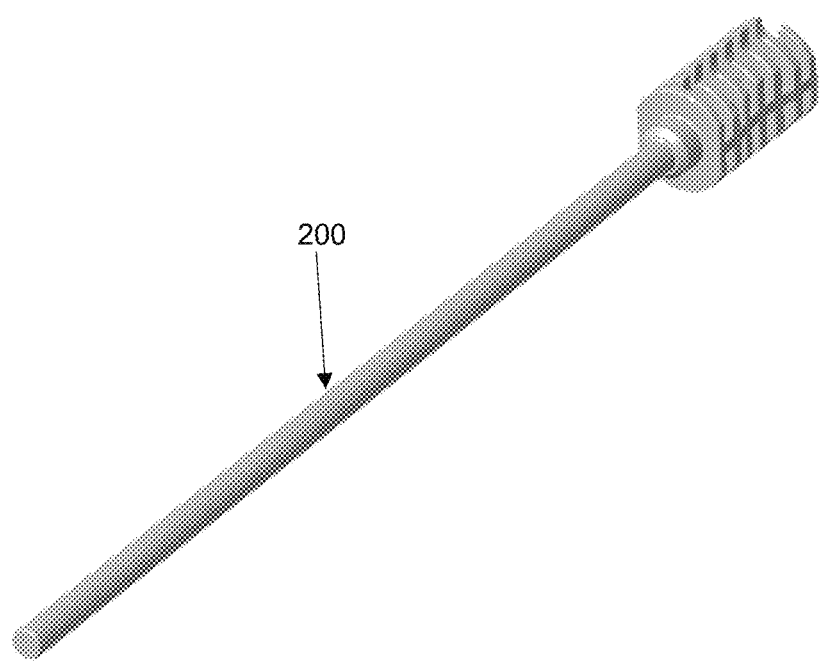
FIG. 13b is a perspective view of an example tamp that can be used with an example bone joint inserter device.

FIG. 13a illustrates an embodiment of inserter device (100) that can accommodate an example tamp (200) (FIG. 13b). Inserter device (100) provides a lumen (25; not shown) to receive tamp (200) for use in delivering material through lumen (25) and impacting tamp (200) such as with a mallet to compact delivered material into a receiving hole in lateral mass of the facet joint. Tamp (200) in this embodiment has a larger end that serves as a stop once it contacts the distal end of inserter device (100).

Figure 13C:
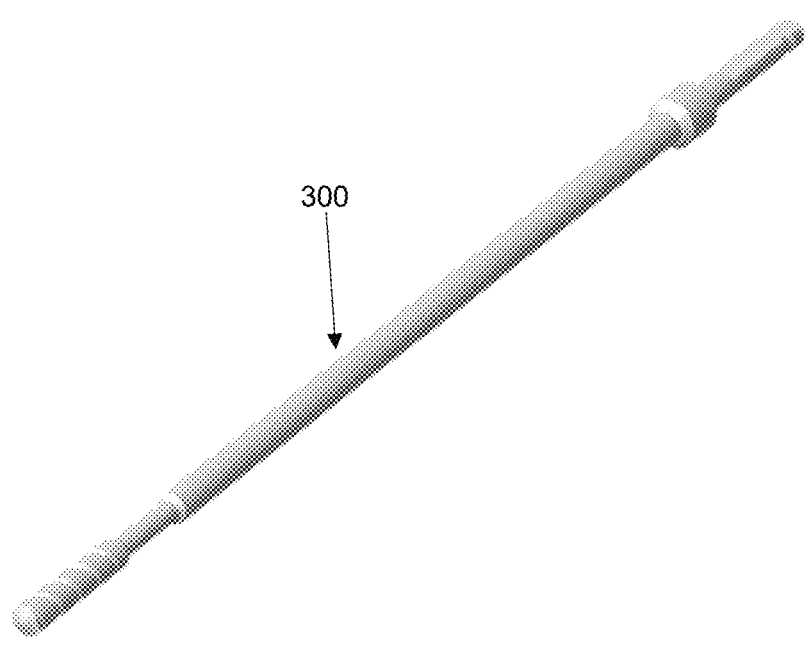
FIG. 13c is a perspective view of an example cutting bit that can be used with an example bone joint inserter device.

FIG. 13c illustrates an example cutting bit (300) that can be employed with inserter device (100). In this embodiment, cutting bit (300) has an enlarged distal section that acts as a stop once it is inserted into lumen (25) of inserter device (100) and pressed toward proximal section (10) and contacts the distal end of inserter device (100).

Figure 13D:
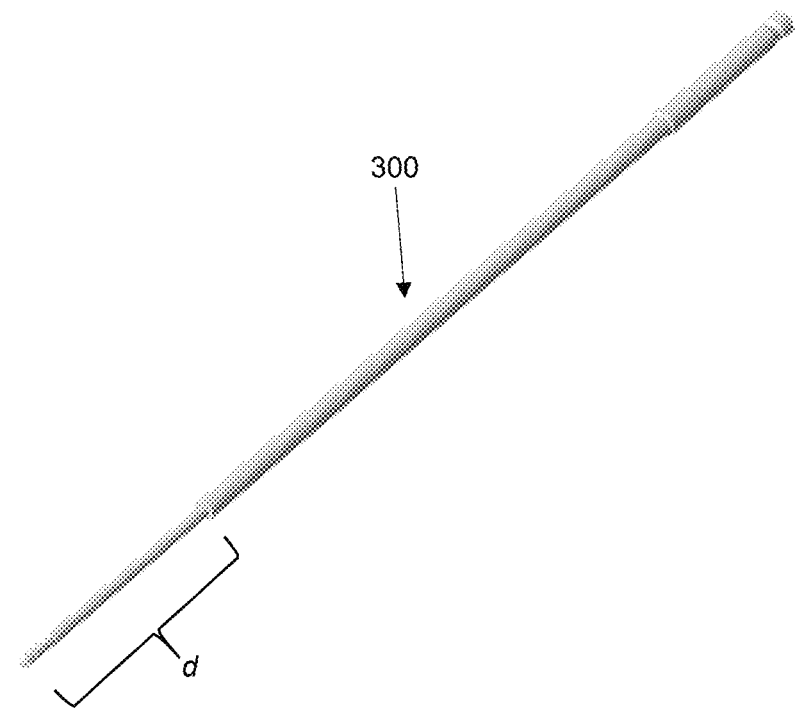
FIG. 13d is a perspective view of an alternative example cutting bit that can be used with an example bone joint inserter device.

FIG. 13d provides an alternative example of a cutting bit (300) that can be employed with inserter device (100). In this embodiment, cutting bit (300) is configured for insertion into a first channel (58), second channel (59), and/or center channel (51) of inserter head (50). The diameter and length of the cutting can be configured to mate with the inserter device channels in order to control the depth of cutting into the target mass. In this example, the distance (d) from the tip of the cutting bit to the initial shoulder can be configured to control drilling depth of the cutting bit (300). For example, distance (d) ranges from about 5 to 50 mm, and can also be adjusted by employing cutting bits of varying distance (d) configurations, and/or via employing one or more collar(s) stops added to the cutting bit (300) to act as a stop where the cutting bit engages the distal portion of the inserter head (50), correspondingly controlling the length of cutting bit (300) protruding from the relevant exit port on the inserter face (70).

Figure 14A:
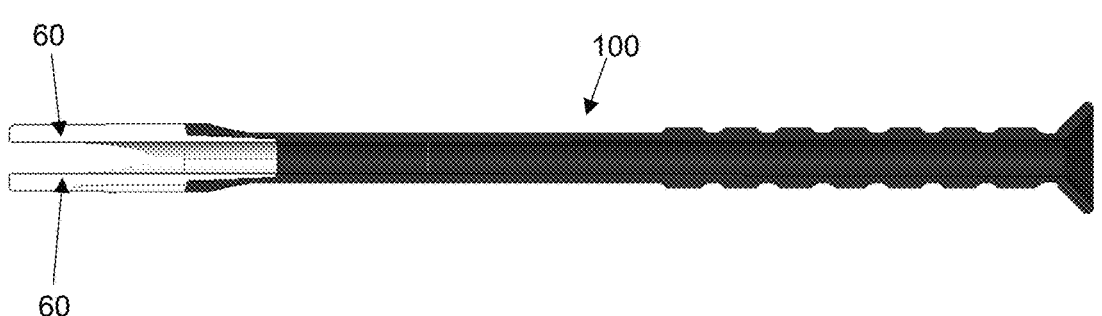
FIG. 14a is a bottom view of an example bone joint inserter device showing the open proximal end of the lumen.
Figure 14B:
FIG. 14b is a side cutaway view of an example bone joint inserter device showing a cutting bit partially housed in the lumen.
Figure 14C:
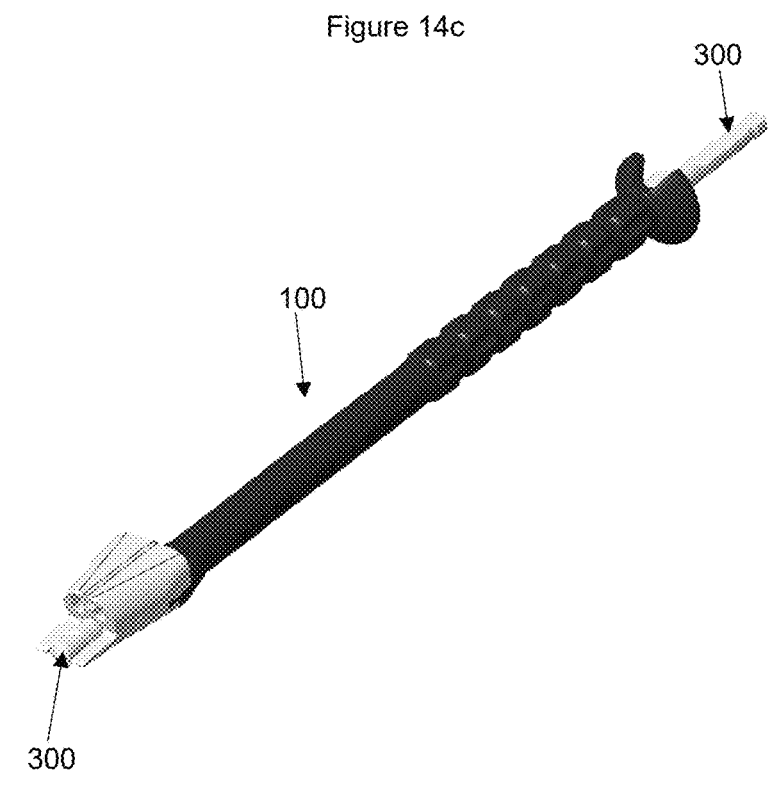
FIG. 14c is a perspective view of an example bone joint inserter device showing a cutting bit fully housed in the lumen and the cutting tip emerging from the proximal section of the bottom of the inserter head.

FIG. 14a provides a bottom view of an example inserter device (100) having a pair of prongs (60) for engaging a facet joint. FIG. 14b provides a side cutaway view of this example of an inserter device (100) with a cutting bit (300) partially inserted into the lumen (25) of inserter device (100). FIG. 14c is a perspective view illustrating this example of a cutting bit (300) fully inserted into the lumen (25) of inserter device (100) so that the tip of cutting bit (300) is shown protruding from proximal section (10) of inserter device (100).

Figure 15A:
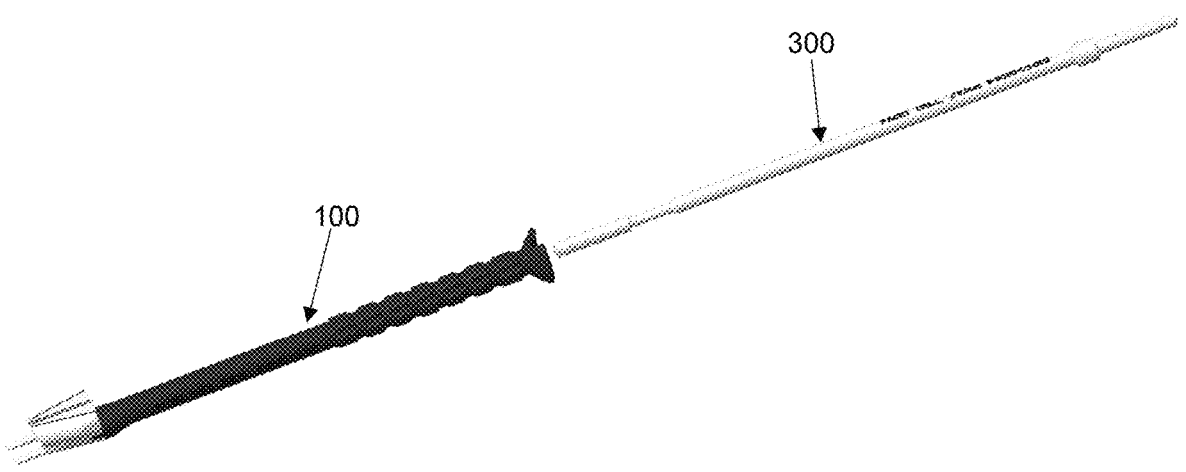
FIG. 15a is a perspective view of an example bone joint inserter device showing a cutting bit prior to entry into distal section of lumen.
Figure 15B:
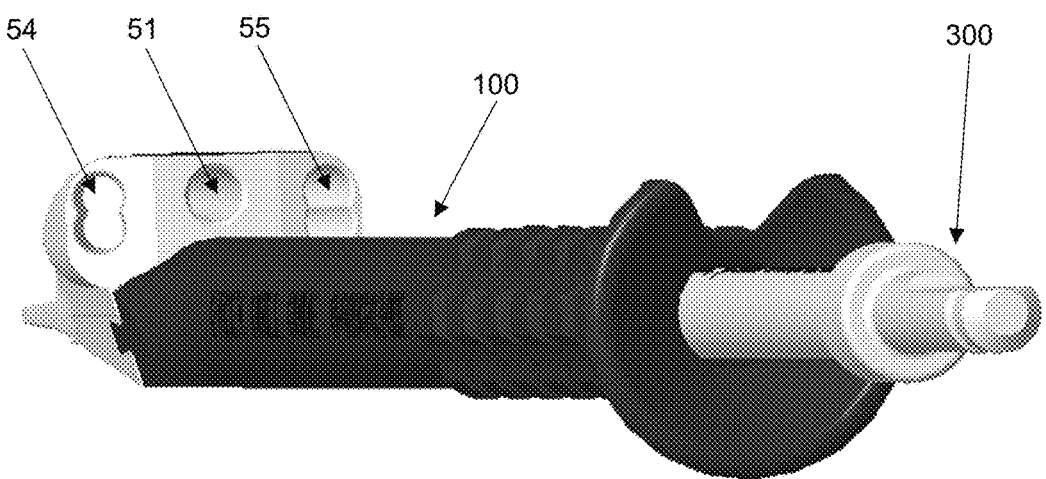
FIG. 15b is a perspective view of an example bone joint inserter device showing a cutting bit partially inserted into distal section of lumen.

FIG. 15a shows an example cutting bit (300) prior to insertion into lumen (25; not shown) of inserter device (100). Similarly, FIG. 15b illustrates an example cutting bit (300) partially inserted into lumen (25) of inserter device (100). This embodiment also provides an example of inserter head (50) having a first entry port (54), a second entry port (55), and a center channel (51). Further, this embodiment demonstrates an example of a double barrel configuration for a first entry port (54) and also for a second entry port (55).

Figure 16A:
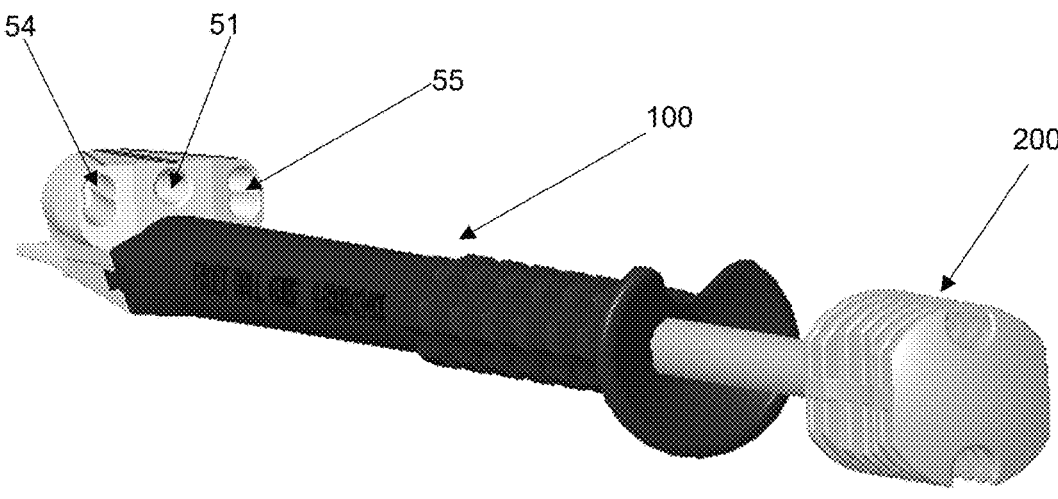
FIG. 16a is a perspective view of an example bone joint inserter device showing a tamp partially inserted into distal section of lumen.
Figure 16B:
FIG. 16b is a side cutaway view of an example bone joint inserter device showing a tamp partially inserted into a lumen of an example bone joint inserter device.
Figure 16C:
FIG. 16c is a side view of an example bone joint inserter device showing a tamp fully inserted into a lumen of an example bone joint inserter device.
Figure 16D:
FIG. 16*d* is a side cutaway view of an example bone joint inserter device showing a tamp fully inserted into a lumen of an example bone joint inserter device.

FIGS. 16a, 16b, 16c and 16d provide an embodiment of an inserter device (100) with an example affiliated tamp (200). FIG. 16a illustrates in a perspective view an embodiment in which tamp (200) is partially inserted into lumen (25) of inserter device (100). FIG. 16b similarly illustrates a cross section view of this embodiment that again shows partial insertion of tamp (200) into inserter device (100). In FIG. 16c, tamp (200) is shown fully inserted into lumen (25) of inserter device (100) in this side view. FIG. 16d provides a side cross section view of tamp (200) fully inserted into lumen (25) of inserter device (100), which also illustrates distal end portion of inserter device (100) in contact with enlarged portion of tamp (200) to prohibit tamp from being further inserted into lumen (25).

In one or more embodiments, the distal end of inserter device (100) can also serve as an impaction surface for the instrument to allow malleting or hammering into the target anatomical area, such as a bone joint. In one or more embodiments, the bone joint includes a vertebral joint, a knee joint, any relevant joint of the arm, leg, foot, elbow, or shoulder, including bone joints of humans or other animals. Inserter device (100) is compatible for use with patients of all ages.

The inserter head (50) is further comprised of superior and inferior portions (80 and 90, respectively). In one or more embodiments, the inserter head (50) is configured with one or more prong(s) (60) that generally extend away from the proximal end of the instrument and can serve to guide the inserter device (100) into the bone joint (such as a facet joint) and orient the inserter device (100) along the axis of the joint (FIG. 3b). These prong(s) (60) can be oriented horizontally, vertically, or a combination of both horizontal and vertical. In one or more embodiments, the prong(s) (60) include various design and functional features, for example, ridges, a rough surface on the top and/or bottom of the prong(s) (60), one or more cutting blades, rasp-like teeth, and the like, to improve orientation and fixation in the joint. Further, the one or more prong(s) (60) can include these and other features to increase or decrease friction of the prong(s) (60) in the surrounding material of the bone joint, thus facilitating ease of entry into the bone joint and potential holding power once the prong(s) (60) reside in the bone joint.

The one or more prong(s) (60) can be in various configurations. For example, the prong(s) (60) can be in the form of forks with a straight or tapered cross-section and extend out from the head (50) of the instrument. In an embodiment, the prong(s) (60) can be a curved shape, such as to engage with and manipulate a curved facet joint. In one example, the prong(s) (60) extend from the head (50) of the inserter device (100) about a maximum of 15 mm. The one or more prong(s) (60) can also be configured as a smooth or tapered blade or a plurality of such blades, and/or can be configured as beveled, tapered, rounded edge, square edge, and the like. In one or more embodiments, the one or more prong(s) (60) are generally located extending from the inferior portion (90) of inserter head (50). In one or more additional embodiments, the one or more prong(s) (60) are generally located extending from the superior portion (80) of inserter head (50). In other embodiments, the one or more prong(s) (60) are generally located extending from an approximate midline area of inserter head (50) between the inferior and superior portions (90 and 80, respectively) of inserter head (50).

Inserter head (50) also comprises an inserter face (70). In one or more embodiments, inserter face (70) may act as a depth stop to prevent over insertion of the one or more prong(s) (60) into the joint. A user engages the joint by sliding the one or more prong(s) (60) into the joint until face (70) engages the corresponding bone or other material near the joint. Face (70) can be oriented a number of ways to improve contact with the neighboring lateral mass anatomy or to set the angle of the instrument relative to the anatomy (FIG. 4). In one embodiment, face (70) is perpendicular to the one or more prong(s) (60) and provides a generally flat surface for the instrument to rest against the upper and/or lower portions of bone defining the joint. In another embodiment, face (70) is tilted proximally towards the lateral mass to contact the anatomy for improved stability. In another embodiment, face (70) is tilted distally away from the lateral mass to accommodate user preference in orienting the one or more prong(s) (60). In yet another embodiment, face (70) is angled to position the inserter device (100) with a medial to lateral trajectory when in the joint. In a further embodiment, face (70) can be multiangled, for example an inserter face (70) with 2 opposing angles for differential placement of face (70) in engaging a target bone site for one or more specific trajectories of an associated entry point into the target mass.

In one or more embodiments, face (70) can have a contact surface that is oriented generally perpendicular to one or more prong(s) (60). In another embodiment, face (70) has a contact surface that is generally curved, and can be radially curved inward or outward, or a combination thereof. In another embodiment, face (70) is a generally smooth surface, or face (70) can have a rough or irregular surface for engagement with bone surface or other lateral mass. In another example, face (70) contains a spike or other protrusion extending from face (70) and engages with bone or other target mass, so that as inserter device (100) is impacted with a mallet or hammer, spikes or other stabilizing element improve stability and fixation of inserter device in the target bone joint. Other face (70) surface configurations for engagement with bone or other anatomical mass are also within the scope of user defined parameters in joint manipulation. Face (70) can also include any combination of these or other configurations.

The superior portion (80) of inserter head (50) can be configured with one or more channels. In one or more embodiments, channels can be located as one or more entry ports at various positions on the distal side of face (70) and continuing through head (50) to emerge from face (70) side of head (50) as one or more exit ports. The distal side of the one or more channel(s) on head (50) provides an entry port into the respective channel, and the proximal side of the one or more channel(s) provides an exit port on face (70). Accordingly, each channel provides one or more entry port(s) for insertion of various instruments, for example, a stylet, a tamp, a tap, a drill bit or other cutting instrument, or any combination thereof. The appropriate instrument inserted into the respective channel(s) is sized accordingly so that channel can provide a guide for the instrument to emerge from the corresponding channel exit port and contact the anatomical mass engaged by the face (70).

For example, one or more first channel(s) (58), one or more second channel(s) (59), and/or one or more center channel(s) (51) may be individually or collectively included, or any combination of such channels. Generally, when included, each channel has a corresponding entry port disposed on the distal side of the inserter head (50), and at least one corresponding exit port on the face (70). In an embodiment, a single entry port of a channel may have more than one corresponding exit port on face (70). Similarly, multiple entry ports may have a corresponding single exit port on face (70).

In one or more embodiments, head (50) can have multiple channel configurations. In one or more embodiments, head (50) can be modular or integrated, so that a user can select an appropriate head (50) with desired channel configuration(s) for a particular use. For example, channels in inserter head (50) can comprise various entry port and/or exit port configurations. As shown, channels can be single entry port and single exit port, vertically or horizontally stacked entry port and exit port, overlapping series of ports (entry and/or exit) with an odd or even number of entry and/or exit ports, and the like, or any combination thereof. In one or more further embodiments, channel(s) can be located in a generally superior position on inserter head (50), and/or in a generally inferior position on inserter head (50), or any combination thereof. In an embodiment, inserter head (50) can provide a center channel (51) or a plurality of center channels (51) in combination with no other channels or with various configurations of lateral channels on inserter head (50). In an embodiment, inserter head (50) can have a single channel on one (lateral) portion of head (50), and at least 2 channels on the other (lateral) portion of inserter head (50). Inserter head (50) can also have a plurality of channels on one lateral side (superior or inferior portion of inserter head (50)), and a single or plurality of channels on the other lateral side (superior or inferior portion of inserter head (50)), again with or without a single center channel (51) or plurality of center channels (51).

In one or more embodiments, the present invention provides single hole, double hole, stacked holes (vertically or horizontally, also referred to as double-barrel holes), offset holes in generally vertical or horizontal orientation, entry port(s) having a slot and a corresponding narrower exit port to allow medial to lateral adjustment of the angle of a cutting bit or stylet inserted into the entry port(s) but further constraining the corresponding exit point to engage a target bone at a specified location.

The superior portion (80) of the inserter head (50) is configured with channels to receive a stylet or slender cutting instrument therethrough at various orientations, the purpose of which is to guide the trajectory of the pilot hole for placement of lateral mass bone anchors. These channels can take many forms that provide different trajectories for the placement of the bone anchors into the lateral mass bone relative to the axis of the Inserter instrument. Generally, these channels can be configured with a medial to lateral trajectory in the axial plane relative to the axis of the instrument. Similarly, in the sagittal plane, the trajectory is generally parallel with the facet joint that the instrument is placed into. Markings on the superior portion (80) of the inserter head (50) can be used to denote the trajectory of the channels to aid in selection of the optimal channel(s).

In one embodiment, the trajectory of the channels in the sagittal orientation is generally fixed parallel with the axis of the instrument such that the stylet or cutting instrument can create a pilot hole trajectory generally parallel with the facet joint. In one or more other embodiments, the angle of the channel is changed relative to the axis of the instrument such that the stylet or cutting instrument is angled (up to) 45° in relation to the central longitudinal axis of the instrument either superiorly or inferiorly towards the prong(s) (60). An "acute angle" is readily understood by one of skill in the art as an angle that is less than 90°. In another embodiment, one or more of the channels has a slot configuration at the entry port with a fixed exit port at the inserter face (70), allowing angular flexibility relative to the access of the inserter device (100) in the sagittal plane.

The medial-lateral trajectory of one or more of the channels can also be configured for different anatomical contact points and surgeon preferences. In one embodiment, the medial to lateral trajectory of the channel is fixed at an angle between about 1 to 45°. In another embodiment, the medial to lateral trajectory of the channel is fixed at an angle between 10 to 25°. In another embodiment, the medial to lateral channel is configured to allow controlled flexibility for the trajectory allowing the surgeon to choose any desired angle within a controlled range. For example, this embodiment can be a slot or other channel geometry that provides a fixed exit port at the inserter face (70), but with a wider opening at the entry port to allow medial-lateral trajectory flexibility (FIG. 7b). In another embodiment, a slot or other channel geometry that provides a fixed exit port at the inserter face (70) provides a wider opening at the entry port to allow inferior-superior trajectory flexibility. In one or more embodiments, the first channel and second channel are located an equal (but opposite) distance from the center line axis of the inserter head (50). For example, the first channel can be oriented at a 25° angle relative to the center line axis of the inserter head (50), and the second channel can be located at a negative –25° angle from the center line axis. Other acute angles for the first and second channel relative to the center line axis of the inserter head (50) are also provided, and the relative first channel and second channel angles are not required to be exactly opposite. For example, the first channel can be oriented at an angle of 20° relative to the center line axis of the inserter head (50), and the second channel can be oriented at an angle of negative –26° relative to the center line axis of the inserter head (50). Accordingly, in one or more embodiments, various combinations of acute angles can be used to orient cutting instrument trajectories, such as by employing modular inserter heads (50) for use with the inserter device (100).

The superior portion of the inserter head (50) can be configured with multiple channels for different anatomical levels and surgeon preferences (FIG. 8). In one embodiment, the inserter head (50) is configured with multiple channels on the left, right, and/or in the center of the inserter head (50). The left and right channels can be configured with a mirrored trajectory, so the instrument can be used on the right and left sides of the spine, respectively. In another embodiment, a central channel is configured parallel with the axis of the inserter device (100) with no medial to lateral angulation. In other embodiments, additional attachments may be added to the inserter head (50) to provide adjustability in terms of the relative degree and/or amount of offset from the joint and/or the angulation relative to the axis of the instrument.

The channels in the superior portion of the inserter head (50) can be configured at various offset distances from the axis of the instrument to allow optimal placement into the lateral mass for each anatomical level and across the complete range of patient anatomy. In one embodiment, the offset distance is between about 2 to 15 mm from the instrument/joint axis. In another embodiment, the offset distance is between about 4 to 7 mm. In another embodiment, each channel may be configured such that it allows the stylet to be used with multiple offsets in the same channel to provide versatility to the surgeon (FIG. 9a). Such an embodiment provides a 'figure 8' shape, for example, to provide two discreet constrained trajectories within the same channel. Other arrangements and configurations with 2 or more discreet constrained trajectories can also be used (FIG. 9b).

The distance that the stylet or slender cutting instrument extends proximally from the inserter face (70) after passing through the channels can be controlled to provide the surgeon with accurate pilot hole depth for their selected bone anchors or other devices. In an embodiment, the proximal extension distance is between about 5 to 30 mm. In one or more embodiments, the distance that the lateral mass drill emerges from the guide feature on the Inserter head (50) is controlled by the user with reference to a depth indicator included on the lateral mass stylet (FIG. 10a). In another embodiment, a secondary interchangeable attachment can be used to provide a physical stop relative to prevent the stylet from advancing past a set distance. Multiple such attachments can be used to provide control to a range of depths (FIG. 10b). In another embodiment, the attachment can be configured so that it is adjustable and provides control over a range of distances.

The size of the channel is generally configured to be used with various stylets known in the art for use in orthopedic surgical applications, including cervical spine procedures. The channels are generally configured to receive a lateral mass stylet sized between about 0.5 to 5 mm.

In an embodiment, channel(s) receive a stylet or slender cutting instrument therethrough for guiding the placement of pilot holes into the target bone for bone anchors while the prong (60) s are in the facet joint. The geometry of these one or more channels can be configured to mate with the aforementioned stylet or cutting instrument to control both the trajectory and depth of insertion into the bone, and ultimately determine the placement of the lateral mass bone anchor.

In one or more embodiments, the inserter device (100) has a lumen (25) extending through the length of the instrument. This lumen (25) can be configured for the insertion of a facet cutting instrument into the distal end of the instrument, through the length of the instrument and out the proximal end into the facet joint or into a surgeon-selected anatomical mass. The lumen (25) is configured so that when the prongs (60) are in the facet joint, the axis of the lumen (25) is generally aligned with the facet joint. The cross-section of the lumen (25) is designed to constrain the facet cutting instrument to provide a repeatable facet joint preparation. In one embodiment, the cross-section of the lumen (25) is generally circular, configured for use with a cylindrical cutting instrument such as a drill, end mill, burr, hole saw or punch. In another embodiment, the lumen (25) is double-barreled (also referred to as a FIG. 8 or a stacked configuration with two overlapping circles. In another embodiment, the lumen (25) is shaped like a slot to allow engagement with a side to side facet cutting instrument. In another embodiment, the lumen (25) is shaped like a square or rectangle to be used with a flat cutting instrument such as a chisel or osteotome.

The lateral mass stylet can be configured in various stylet tip geometries for creating the desired trajectory in the lateral mass bone and mating with the channel in the Inserter head (50). This includes a trochar tip stylet, a diamond tip stylet, an end mill tip, a burr tip, a beveled tip stylet, a drill tip and the like. Stylets employed with the Inserter device (100) may be replaceable, disposable, or reusable.

The facet joint cutting tool stylet can be configured to create a repeatable defect in the facet joint and to mate with the lumen (25) of the Inserter Guide. For example, various rotary cutting instruments such as drills, end mills, burrs, hole saws and coring instruments, and the like can be used. In other embodiments, a chisel, osteotome or impaction style cutter can be employed. The facet joint cutting tool employed with the Inserter device (100) can be replaceable, disposable, or reusable.

Components of the presently described device may be manufactured of various materials. Example materials include various metals and alloys thereof, including stainless steel, titanium, aluminum, and combinations thereof. Metals used in materials of construction for the bone anchor insertion device components also include nitinol (nickel titanium), and austenitic steels such as Nitronic 50 and Nitronic 60, for example. Silicone and silicone blends may also be used to fabricate one or more of the components in the device. Further, materials of construction for one or more of the components of the present bone anchor insertion device include fluoropolymer, other plastics, and composite materials. Examples are: PEEK (polyetheretherketone); PPS (polyphenylene sulfide); PPSU (polyphenylsulfone); FEP (fluorinated ethylene propylene); PCTFE (polychlorotrifluoroethylene); PFA (perfluoroalkoxy); ETFE (ethylene tetrafluoroethylene); ECTFE (ethylene chlorotrifluoroethylene); PP (polypropylene); ABS (acrylonitrile butadiene styrene); PARA (polyacrylamide); glass-fiber reinforced polyacrylamide (IXEF-PARA); combinations of these representative materials, and the like.

In particular, materials of construction employed in one or more of the components of the Inserter device (100) are able to withstand various autoclaving procedures, including parameters such as saturated steam under pressure (~1 atm), along with concomitant autoclave chamber temperatures ranging from about 100° C. to 150° C. for about 15 to 60 minutes. Additionally, the materials of construction employed in one or more of the components in Inserter device (100) are able to withstand sterilization from other means of terminal sterilization such as, and not limited to, ethylene oxide, electron beam irradiation and gamma irradiation. Materials of construction can withstand one or more of such sterilization techniques and parameters, though not necessarily all such sterilization procedures.

Exemplary embodiments described herein provide an overall understanding of the principles of the structure, function, manufacture, and use of the devices and methods disclosed herein. One or more examples of these embodiments are illustrated in the accompanying drawings. One of skill in the art will understand that the devices and methods described herein and illustrated in the accompanying drawings are non-limiting exemplary embodiments. Features illustrated and/or described in connection with one exemplary embodiment may be combined with the features of one or more other embodiments; such modifications and variations are intended to be included within the scope of the present invention.

Methods and devices for preparing the cervical facet joint for fusion and guiding the bone anchor devices and/or bone anchor assemblies into bone are provided herein. Use of these instruments can provide a means to eliminate one or more of the steps in a conventional bone anchor installation procedure, improving surgical efficiency and patient safety.

One of ordinary skill in the art will readily understand that any ordering of method steps implied by the drawings or description herein is not to be construed as limiting or requiring the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

Any publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims. The devices and methods disclosed herein can be used in minimally-invasive surgery and/or open surgery. While the devices and methods disclosed herein are generally described, it will be appreciated that the methods and devices disclosed herein can be used with any human or animal bone, implant, non-living object, and the like. Also, it should be understood that numerous changes may be made within the spirit and scope of the inventive concepts described. Accordingly, it is intended that the invention should not be limited to the described embodiments, but that it have the full scope defined by the following claims.

The invention claimed is:

1. A method for implanting a bone anchor device comprising:
   providing a bone joint inserter device comprising:
      (a) a proximal section comprising an inserter head, wherein said inserter head comprises:
         a face;
         at least one prong;
         a first channel comprising a first entry port and a first exit port, wherein said first entry port is at least as wide as said first exit port, and wherein said first channel is oriented at a first acute angle relative to a center line of said inserter head; and
         a second channel comprising a second entry port and a second exit port, wherein said second entry port is at least as wide as said second exit port, and wherein said second channel is oriented at a second acute angle relative to the center line of said inserter head;
      (b) a distal section comprising a notch operably receiving and positively orienting a drill, a cutting tool, a stylet, or a tamp;
      (c) a shaft disposed between said proximal section and said distal section; and
      (d) a lumen extending along a central axis of the bone joint inserter device from said distal section through said shaft and through said proximal section;
   creating an access opening to expose a target cervical facet joint;
   inserting said at least one prong of said inserter head into the target cervical facet joint;
   aligning said face of said inserter head with a target bone surface of the target cervical facet joint;
   introducing a cutting instrument through at least one of said first channel and said second channel;

impacting the target bone surface with said cutting instrument to produce a receiving site for said bone anchor device;

disengaging said cutting instrument from said target bone surface;

withdrawing the bone joint inserter device; and inserting the bone anchor device into the receiving site on the target bone.

2. The method of claim 1, wherein said proximal section is fixedly interconnected to said shaft, and said shaft is fixedly interconnected to said distal section.

3. The method of claim 1, wherein said face comprises a contact surface shape comprising flat, angled, curved, concave, convex, or a combination thereof.

4. The method of claim 1, wherein said at least one prong comprises an end shape comprising pointed, tapered, beveled, chiseled, blunt, rounded, or square.

5. The method of claim 1, wherein the notch operably orients a compatible device substantially parallel to the central axis of said inserter device.

6. The method of claim 1, wherein said distal section comprises a lumen entry port shape comprising round, rectangular, square or elliptical.

7. The method of claim 1, wherein a width of said first entry port is wider than said first exit port, and a width of said second entry port is wider than said second exit port.

8. A method for implanting a bone anchor device comprising:

providing a bone joint inserter device comprising:
    (a) a proximal section comprising an inserter head, wherein said inserter head comprises:
    a face;
    at least two prongs;
    a first channel comprising a first entry port and a first exit port, wherein said first entry port is at least as wide as said first exit port, and wherein said first channel is oriented at a first acute angle relative to a center line of said inserter head; and
    a second channel comprising a second entry port and a second exit port, wherein said second entry port is at least as wide as said second exit port, and wherein said second channel is oriented at a second acute angle relative to the center line of said inserter head;
    (b) a distal section comprising a notch operably receiving and positively orienting a drill, a cutting tool, a stylet, or a tamp;
    (c) a shaft disposed between said proximal section and said distal section; and
    (d) a lumen extending along a central axis of the bone joint inserter device from said distal section through said shaft and through said proximal section;

creating an access opening to expose a target cervical facet joint;

inserting said at least two prongs of said inserter head into the target cervical facet joint;

aligning said face of said inserter head with a target bone surface of the target cervical facet joint;

introducing a cutting instrument through at least one of said first channel and said second channel;

impacting the target bone surface with said cutting instrument to produce a receiving site for said bone anchor device;

disengaging said cutting instrument from said target bone surface;

withdrawing the bone joint inserter device; and inserting the bone anchor device into the receiving site on the target bone.

9. The method of claim 8, wherein said proximal section is fixedly interconnected to said shaft, and said shaft is fixedly interconnected to said distal section.

10. The method of claim 8, wherein said face comprises a contact surface shape comprising flat, angled, curved, concave, convex, or a combination thereof.

11. The method of claim 8, wherein said at least two prongs comprise an end shape comprising pointed, tapered, beveled, chiseled, blunt, rounded, or square.

12. The method of claim 8, wherein the notch operably orients a compatible device substantially parallel to the central axis of said inserter device.

13. The method of claim 8, wherein said distal section comprises a lumen entry port shape comprising round, rectangular, square, or elliptical.

14. The method of claim 8, wherein a width of said first entry port is wider than said first exit port, and a width of said second entry port is wider than said second exit port.

15. A method for implanting a bone anchor device comprising:

providing a bone joint inserter device comprising:
    (a) a proximal section comprising an inserter head, wherein said inserter head comprises:
    a face;
    at least one prong;
    a first channel comprising a first entry port and a first exit port, wherein said first entry port is at least as wide as said first exit port, and wherein said first channel is oriented at a first acute angle relative to a center line of said inserter head; and
    a second channel comprising a second entry port and a second exit port, wherein said second entry port is at least as wide as said second exit port, and wherein said second channel is oriented at a second acute angle relative to the center line of said inserter head;
    a center channel comprising a central entry port and a central exit port, wherein said central entry port is at least as wide as said central exit port, and wherein said center channel is disposed between said first channel and said second channel;
    (b) a distal section comprising a notch operably receiving and positively orienting a drill, a cutting tool, a stylet, or a tamp;
    (c) a shaft disposed between said proximal section and said distal section; and
    (d) a lumen extending along a central axis of the bone joint inserter device from said distal section through said shaft and through said proximal section;

creating an access opening to expose a target cervical facet joint;

inserting said at least one prong of said inserter head into the target cervical facet joint;

aligning said face of said inserter head with a target bone surface of the target cervical facet joint;

introducing a cutting instrument through at least one of said first channel, said second channel, and said center channel;

impacting the target bone surface with said cutting instrument to produce a receiving site for said bone anchor device;

disengaging said cutting instrument from said target bone surface;

withdrawing the bone joint inserter device; and inserting the bone anchor device into the receiving site on the target bone.

16. The method of claim 15, wherein said proximal section is fixedly interconnected to said shaft, and said shaft is fixedly interconnected to said distal section.

17. The method of claim 15, wherein said face comprises a contact surface shape comprising flat, angled, curved, concave, convex, or a combination thereof.

18. The method of claim 15, wherein said at least one prong comprises an end shape comprising pointed, tapered, beveled, chiseled, blunt, rounded, or square.

19. The method of claim 15, wherein a width of said first entry port is wider than said first exit port, and a width of said second entry port is wider than said second exit port.

20. The method of claim 15, wherein said first entry port comprises two holes arranged in a vertically stacked configuration, and said second entry port comprises two holes arranged in a vertically stacked configuration.

* * * * *